(12) United States Patent
Schraga

(10) Patent No.: US 8,257,380 B2
(45) Date of Patent: Sep. 4, 2012

(54) ADJUSTABABLE DISPOSABLE/SINGLE-USE LANCET DEVICE AND METHOD

(75) Inventor: Steven Schraga, Surfside, FL (US)

(73) Assignee: Stat Medical Devices, Inc., North Miami, FL (US)

( * ) Notice: Subject to any disclaimer, the term of this patent is extended or adjusted under 35 U.S.C. 154(b) by 2739 days.

(21) Appl. No.: 10/878,390

(22) Filed: Jun. 29, 2004

(65) Prior Publication Data

US 2005/0288699 A1    Dec. 29, 2005

(51) Int. Cl.
*A61B 17/14* (2006.01)
(52) U.S. Cl. .......................................... 606/181
(58) Field of Classification Search .......... 606/180–182, 606/136–139; 600/583
See application file for complete search history.

(56) References Cited

U.S. PATENT DOCUMENTS

| | | |
|---|---|---|
| 676,678 A | 6/1901 | Ellifrits |
| 1,135,465 A | 4/1915 | Pollock |
| 2,848,809 A | 2/1956 | Crowder |
| 3,589,213 A | 6/1971 | Gourley |
| 4,139,011 A | 2/1979 | Benoit et al. |
| 4,203,446 A | 5/1980 | Höfert et al. |
| 4,257,561 A | 3/1981 | McKinney |
| 4,388,925 A | 6/1983 | Burns |
| 4,426,105 A | 1/1984 | Plaquin et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,628,929 A | 12/1986 | Intengan et al. |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |

(Continued)

FOREIGN PATENT DOCUMENTS

CA            523078           3/1956
(Continued)

OTHER PUBLICATIONS

Sutor et al., "Bleeding from Standardized Skin Punctures: Automated Technic for Recording Time, Intensity, and Pattern of Bleeding", *A.J.C.P.*, vol. 55, pp. 541-549 (May 1971).

*Primary Examiner* — Ryan Severson
*Assistant Examiner* — Jonathan W Miles
(74) *Attorney, Agent, or Firm* — Greenblum & Bernstein, P.L.C.

(57) ABSTRACT

Adjustable Single-use lancet device that includes a body. A trigger is mounted to the body. A skin engaging end includes a lancet opening through which a lancet needle extends. A holding member is movably mounted within the body and includes a front end a rear end. The front end receives a lancet needle. A stop surface moves with the holding member. A cam disk includes cam surfaces which can be contacted by the stop surface. The cam disk is configured to rotate at least partially. The cam disk rotates about an axis that is not parallel to an axis running through at least one of the lancet opening and the holding member. Once caused to move to the extended position by the trigger, the holding member is prevented from moving back to the retracted position. This Abstract is not intended to define the invention disclosed in the specification, nor intended to limit the scope of the invention in any way.

36 Claims, 30 Drawing Sheets

U.S. PATENT DOCUMENTS

| | | | |
|---|---|---|---|
| 4,869,249 A | 9/1989 | Crossman et al. | |
| 4,895,147 A | 1/1990 | Bodicky et al. | |
| 4,924,879 A | 5/1990 | O'Brien | |
| 4,976,724 A | 12/1990 | Nieto et al. | |
| 4,990,154 A | 2/1991 | Brown et al. | |
| 5,074,872 A | 12/1991 | Brown et al. | |
| 5,147,375 A | 9/1992 | Sullivan et al. | |
| 5,212,879 A | 5/1993 | Biro et al. | |
| 5,269,799 A | 12/1993 | Daniel | |
| 5,282,822 A | 2/1994 | Macors et al. | |
| 5,304,193 A * | 4/1994 | Zhadanov | 606/182 |
| 5,318,583 A * | 6/1994 | Rabenau et al. | 606/182 |
| 5,318,584 A | 6/1994 | Lange et al. | |
| 5,324,303 A | 6/1994 | Strong et al. | |
| 5,350,392 A | 9/1994 | Purcell et al. | |
| 5,356,420 A | 10/1994 | Czernecki et al. | |
| 5,366,470 A | 11/1994 | Ramel | |
| 5,395,388 A | 3/1995 | Schraga | |
| 5,423,847 A | 6/1995 | Strong et al. | |
| 5,439,473 A | 8/1995 | Jorgensen | |
| 5,454,828 A | 10/1995 | Schraga | |
| 5,464,418 A | 11/1995 | Schraga | |
| 5,476,101 A | 12/1995 | Schramm et al. | |
| 5,509,345 A | 4/1996 | Cyktich | |
| 5,518,004 A | 5/1996 | Schraga | |
| 5,554,166 A | 9/1996 | Lange et al. | |
| 5,569,286 A | 10/1996 | Peckham et al. | |
| 5,569,287 A | 10/1996 | Tezuka et al. | |
| D376,203 S | 12/1996 | Schraga | |
| 5,613,978 A | 3/1997 | Harding | |
| 5,628,764 A | 5/1997 | Schraga | |
| 5,628,765 A | 5/1997 | Morita | |
| 5,643,306 A | 7/1997 | Schraga | |
| 5,730,753 A | 3/1998 | Morita | |
| 5,741,288 A | 4/1998 | Rife | |
| RE35,803 E | 5/1998 | Lange et al. | |
| 5,797,942 A | 8/1998 | Schraga | |
| 5,873,887 A | 2/1999 | King et al. | |
| 5,879,367 A | 3/1999 | Latterell et al. | |
| 5,908,434 A | 6/1999 | Schraga | |
| 5,916,230 A | 6/1999 | Brenneman et al. | |
| 5,984,940 A | 11/1999 | Davis et al. | |
| 6,022,366 A | 2/2000 | Schraga | |
| 6,045,567 A | 4/2000 | Taylor et al. | |
| 6,056,765 A | 5/2000 | Bajaj et al. | |
| 6,071,294 A | 6/2000 | Simons et al. | |
| D428,150 S | 7/2000 | Ruf et al. | |
| 6,136,013 A | 10/2000 | Marshall et al. | |
| 6,152,942 A | 11/2000 | Brenneman et al. | |
| 6,156,050 A | 12/2000 | Davis et al. | |
| 6,156,051 A | 12/2000 | Schraga | |
| 6,168,606 B1 | 1/2001 | Levin et al. | |
| 6,183,489 B1 | 2/2001 | Douglas et al. | |
| 6,190,398 B1 | 2/2001 | Schraga | |
| 6,192,891 B1 | 2/2001 | Gravel et al. | |
| 6,197,040 B1 | 3/2001 | Le Vaughn et al. | |
| 6,210,420 B1 | 4/2001 | Mauze et al. | |
| 6,221,089 B1 | 4/2001 | Mawhirt | |
| 6,228,100 B1 | 5/2001 | Schraga | |
| 6,258,112 B1 | 7/2001 | Schraga | |
| 6,283,982 B1 | 9/2001 | Levaughn et al. | |
| 6,306,152 B1 | 10/2001 | Verdonk et al. | |
| 6,322,574 B1 | 11/2001 | Lloyd et al. | |
| 6,322,575 B1 | 11/2001 | Schraga | |
| 6,332,871 B1 | 12/2001 | Douglas et al. | |
| 6,346,114 B1 | 2/2002 | Schraga | |
| 6,364,889 B1 | 4/2002 | Kheiri et al. | |
| 6,379,317 B1 | 4/2002 | Kintzig et al. | |
| 6,409,740 B1 | 6/2002 | Kuhr et al. | |
| 6,419,661 B1 | 7/2002 | Kuhr et al. | |
| 6,451,040 B1 | 9/2002 | Purcell | |
| 6,464,649 B1 | 10/2002 | Duchon et al. | |
| 6,506,168 B1 | 1/2003 | Fathallah et al. | |
| 6,514,270 B1 | 2/2003 | Schraga | |
| 6,540,762 B1 | 4/2003 | Bertling | |
| 6,558,402 B1 | 5/2003 | Chelak et al. | |
| 2003/0050656 A1 * | 3/2003 | Schraga | 606/182 |

FOREIGN PATENT DOCUMENTS

| | | |
|---|---|---|
| EP | 0061102 | 9/1982 |
| EP | 0137975 | 4/1985 |
| EP | 0189117 | 7/1986 |
| EP | 0885590 | 12/1998 |
| EP | 0904731 | 3/1999 |
| EP | 1074219 | 2/2001 |
| FR | 1126718 | 11/1956 |

* cited by examiner

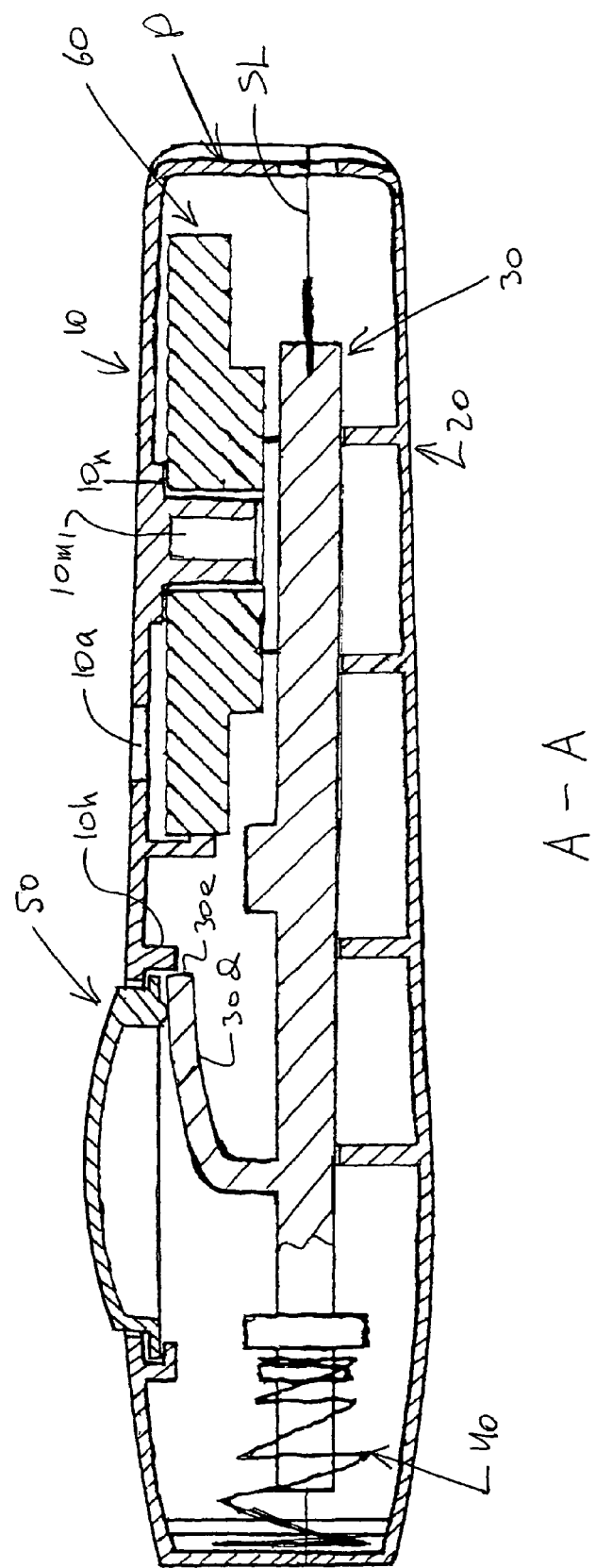

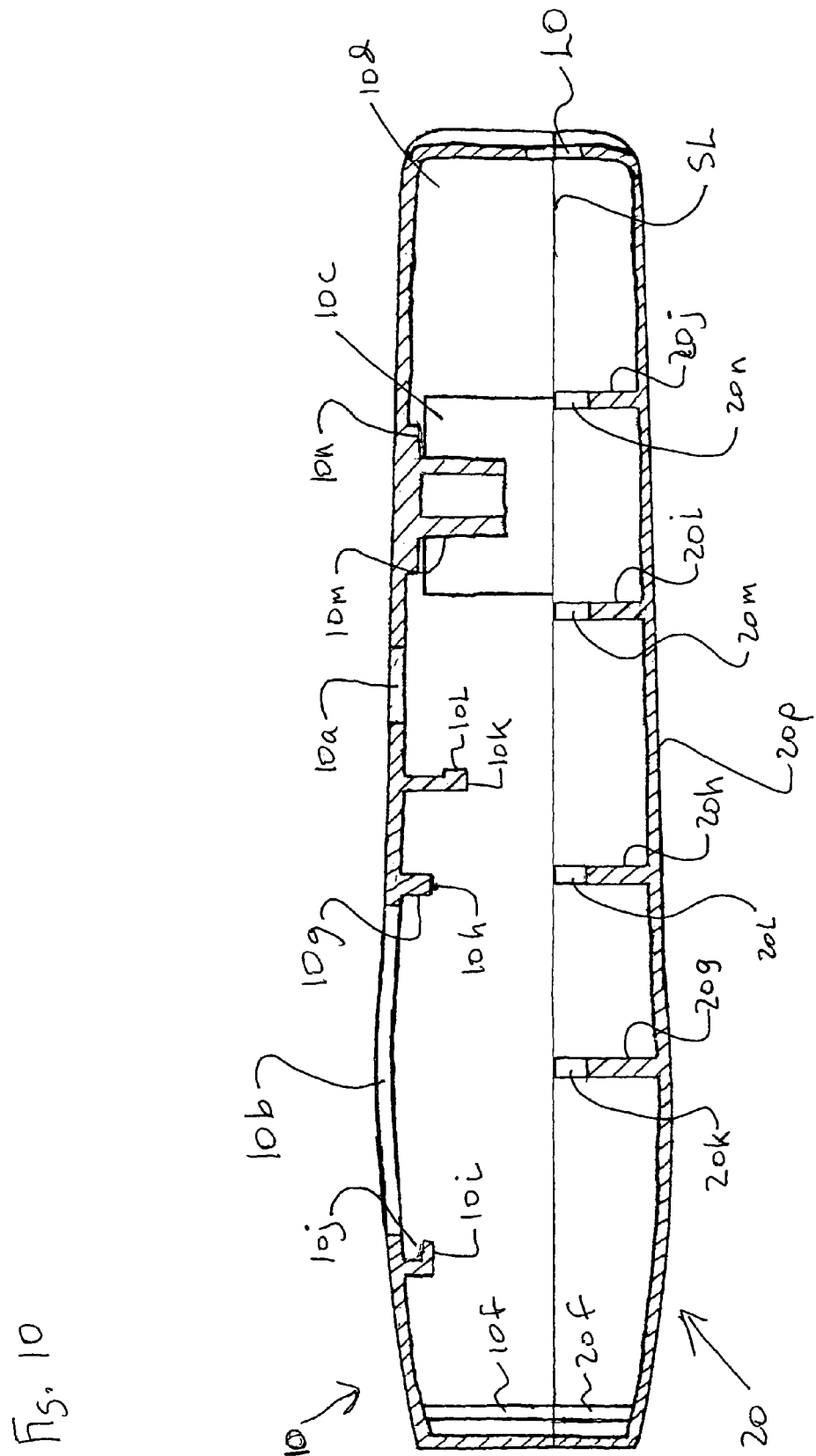

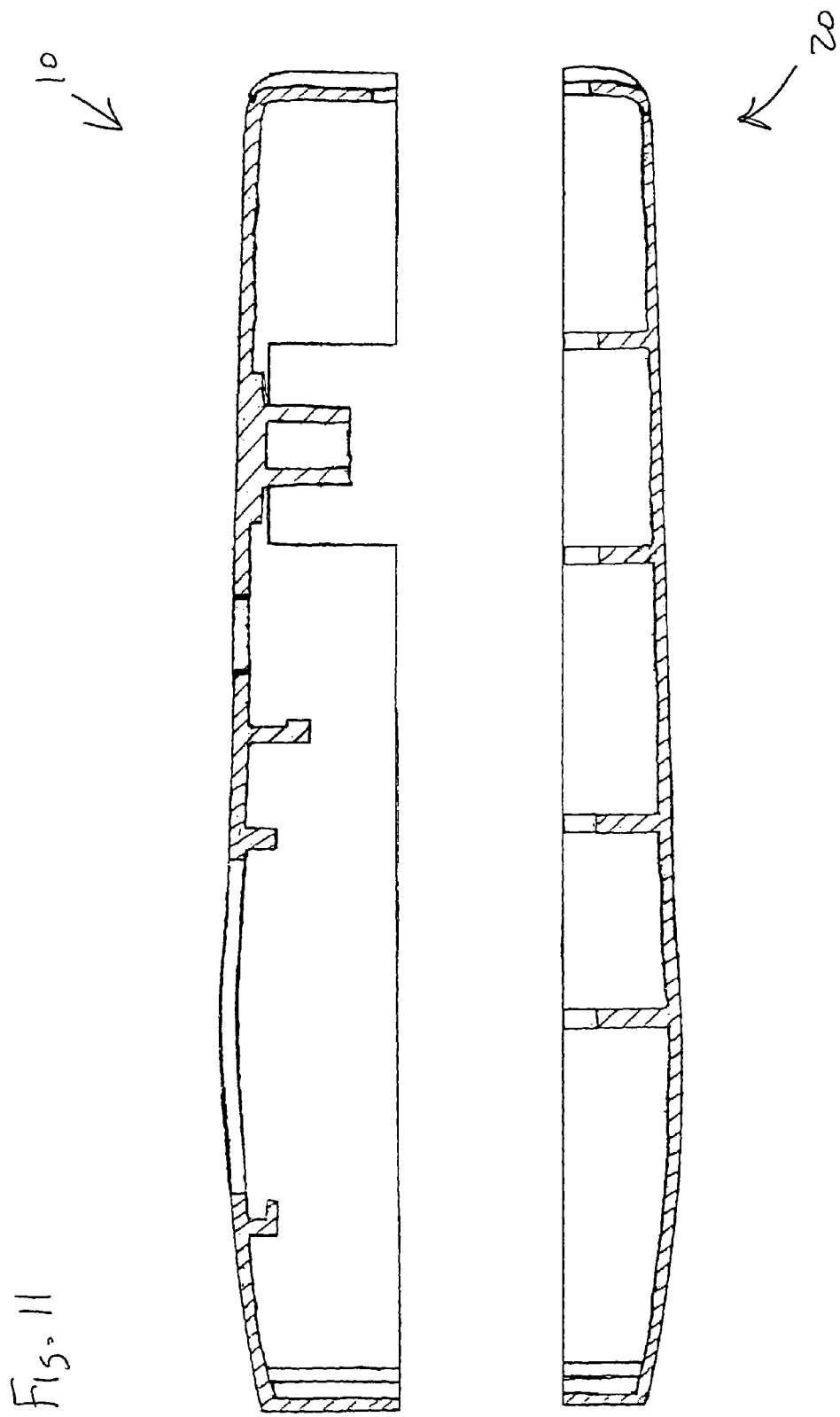

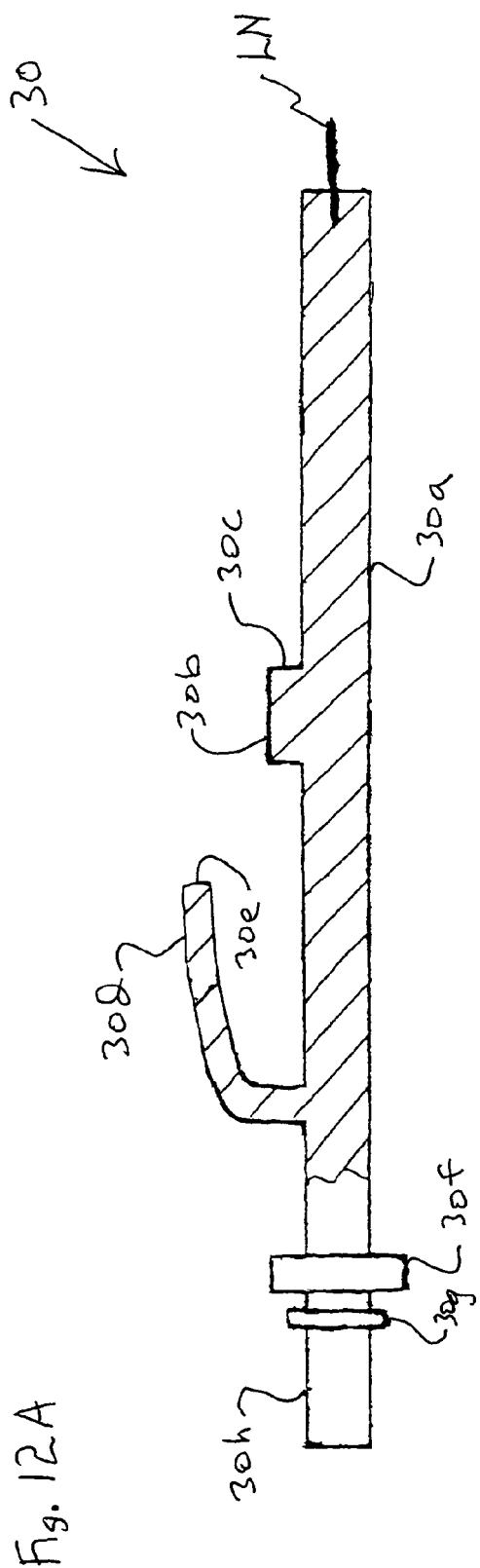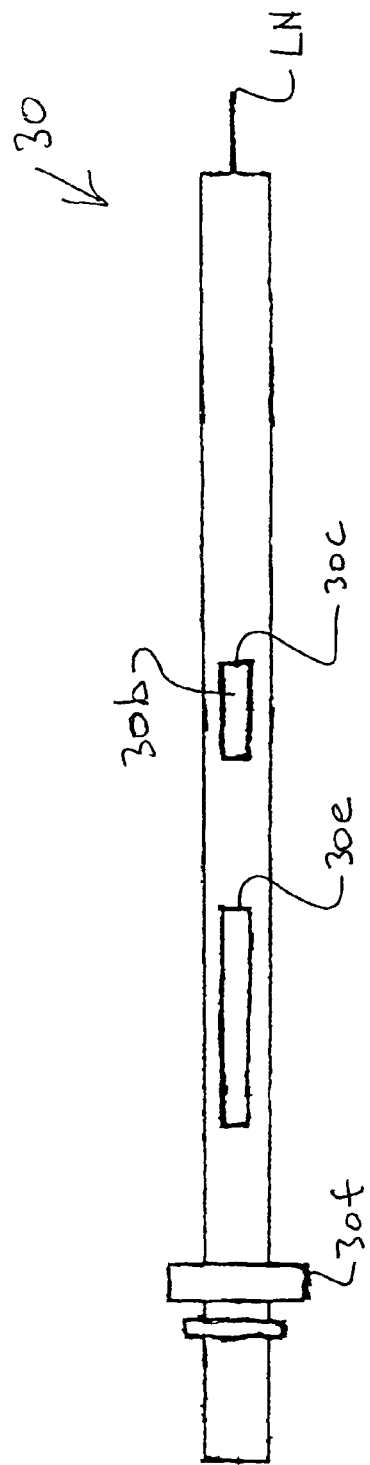

C-C

ADJUSTABABLE DISPOSABLE/SINGLE-USE LANCET DEVICE AND METHOD

BACKGROUND OF THE INVENTION

1. Field of the Invention

The invention relates to a disposable and/or single-use lancet device having an adjusting capability, and to a method of using a disposable and/or single-use lancet device. In particular, the invention relates to a lancet device which may be both disposable, i.e., which can be used once and discarded, and which also utilizes an adjustable depth of penetration.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. With this device, the user must remove one tip having a set depth and replace it with another having a different set depth. This, of course, creates the problem of storing the replaceable tips, which if not properly done, may result in their misplacement, damage, contamination, or the like. Additionally, such penetration depth adjustment is not available on disposable or single-use lancet devices.

An improved device would allow the user to easily adjust the depth of penetration of a single-use lancet and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have thicker skin. By adjusting the depth of puncture so that the depth is no greater than necessary for extracting a required amount of blood, any pain experienced by the user may be minimized.

Lancets having an adjustable tip are known per se. For example, U.S. Pat. No. 4,469,110 to SLAMA discloses a mechanism which adjusts the penetration depth by rotating a threaded sleeve relative to a body. The SLAMA device is characterized as a "single bottom" device which employs a threaded design which can be expensive to manufacture. Moreover, such a device may require the user to rotate the threaded sleeve up to 360 degrees and more in order to attain the proper depth setting. Further, such a threaded resign is prone to inadvertent setting changes since there is nothing but frictional engagement between the mating threads to maintain the adjustment setting.

U.S. Pat. No. 4,895,147 to BODICKY et al. functions in a similar manner to the device in SLAMA and therefore suffers from similar disadvantages.

U.S. Pat. Nos. 5,464,418, 5,797,942, 5,908,434, 6,156,051 and 6,530,937 to SCHRAGA also disclose similar lancet devices and are hereby incorporated herein by reference as though set forth in full herein.

As disclosed in U.S. Pat. No. 5,908,434, the lancet device has a body portion which encloses a lancet and a lancet firing mechanism. The lancet typically has a needle extending therefrom and is caused to move towards the tip of the device by a trigger or firing mechanism. The lancet device forces the needle, by virtue of the needle being fixed thereto, out of the device by some distance or depth so that the needle can penetrate the skin of the user. The function of this firing mechanism and the lancet body design is disclosed in each of U.S. Pat. No. 5,797,942 and U.S. Pat. No. 5,908,434. These patents are incorporated by reference herein in their entirety and are therefore only briefly discussed herein.

Lancet devices are used to penetrate and puncture the skin in order to allow the taking of a blood sample for testing. More expensive lancet devices have been provided with penetration depth adjustment. However, typical disposable or single-use lancet devices have not utilized depth adjustment. The present device allows the user to control the depth of this penetration in a disposable lancet device by utilizing a simple and/or inexpensive adjustment mechanism. What is needed is an inexpensive single-use lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices.

Thus, while advances have been made, there is a continuing need for a lancet device which provides for convenient, reliable and easy adjustment of penetration depth and which is inexpensively made (i.e., by utilizing fewer parts or components) so that it can be economically used a single time and thereafter disposed of.

SUMMARY OF THE INVENTION

According to one aspect of the invention there is provided a disposable and/or single-use lancet device that includes a body. A trigger is preferably mounted to the body. A front cover includes a skin engaging end that includes a lancet opening through which a lancet needle extends. A holding member is movably mounted within the body and comprises a front end and a rear end. The front end is configured to receive a lancet or lancet needle. A stop surface moves with the holding member. A cam disk includes cam surfaces which can be contacted by the stop surface. The cam disk is configured to rotate at least partially. The cam disk rotates about an axis that is not parallel to an axis running through at least one of the lancet opening and the holding member.

The lancet device may further preferably comprise a spring for biasing the back cap towards an original position. The lancet device may further preferably comprise a spring for biasing the holding member towards an extended position and for moving the holding member in an opposite direction. The springs may preferably be arranged to surround a portion of the holding member. The spring may have one coupled to the lancet body and another end coupled to the holding member.

The trigger may preferably be movably mounted to the body. The holding member may preferably comprise a projection that includes the stop surface. The holding member may preferably comprise an integrally formed projection that includes the stop surface. A front end of the lancet device may preferably comprise an opening that is configured to removably receive and/or allow passage therethrough of the lancet.

The lancet device may preferably further comprise a deflecting member configured to be deflected by the trigger. The deflecting member may preferably be coupled to the holding member. The deflecting member may preferably comprise a stop surface that contacts a surface of a holding projection extending inwardly from the body. The cam disk may comprise indicia. The cam surfaces may preferably be arranged on a cam section of the cam disk. The cam section may preferably be disposed on a side of the cam disk that is opposite a side that includes the indicia. The cam disk may preferably comprise a centrally disposed opening that is mounted to a journal within the body.

The journal may preferably be coupled to the body. The journal may preferably extend inwardly from the body. The journal may preferably comprise a center axis that is generally perpendicular to the axis running through the holding member. The cam disk may preferably rotate about an axis that is generally perpendicular to an axis running through at least one of the lancet opening and the holding member. The cam disk may preferably be disposed between the trigger and a lancet opening. The body may preferably comprise a two piece body. The cam disk may preferably be coupled to one of the two pieces of the two piece body. The lancet device may further comprise a back trigger movably mounted to the two piece body. The body may preferably comprise at least one curved side indentation through which the cam disk protrudes. The body may comprise preferably two oppositely arranged curved side indentations through which portions of the cam disk protrude. The body may preferably comprise a mechanism for viewing indicia of the cam disk. The mechanism for viewing indicia of the cam disk may preferably comprise an opening. The lancet device may preferably further comprise a retaining element for one of axially retaining the cam disk and securing the cam disk to the body.

The invention also provides a method of puncturing a surface of skin using the single-use lancet device described above, wherein the method comprises adjusting a set depth of penetration of the needle by moving the cam disk to a desired set position, disposing the skin engaging end of the lancet device against a user's skin, triggering the trigger to cause the lancet needle to penetrate the user's skin, and preventing the holding member from moving to a retracted position and/or from being caused to move by the trigger, wherein the puncture allows a blood sample to be taken.

The invention also provides a method of using the lancet device described above, wherein the method comprises rotating the cam disk to a desired set position, moving the holding member to a retracted position, maintaining the holding member in the retracted position until the trigger is triggered, disposing the skin engaging end of the lancet device against a user's skin, triggering the trigger to cause movement of the holding member, and preventing the holding member from again moving to a retracted position and/or from being caused to move by the trigger.

The invention also provides a single-use lancet device, that includes a body, a trigger, a front cover comprising a skin engaging end that includes a lancet opening through which a lancet needle extends. A holding member is movably mounted within the body and comprising a front end a rear end. The front end is configured to receive a lancet. A stop projection is coupled to the holding member. A cam disk comprises indicia and cam surfaces which can be contacted by the stop projection. The cam disk is configured to rotate at least partially. The cam disk is mounted to a projection that extends inwardly from the body.

The invention also provides a single-use and/or disposable lancet device comprising a body, a trigger, a front cover comprising a skin engaging end that includes a lancet opening through which a lancet needle extends. A holding member is movably mounted within the body and comprising a front end a rear end. The front end is configured to receive a lancet. A removable tab is configured to move the holding member to a retracted position. A stop surface is coupled to the holding member. A cam disk is at least partially arranged within the body. The cam disk comprises indicia and cam surfaces which can be contacted by the stop projection. The cam disk is configured to rotate at least partially. The cam disk protrudes from at least one side wall of the body.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 9 shows an enlarged side cross-section view of the embodiment shown in FIG. 1. The device is shown with lancet holding member in the armed and/or fully retracted and/or trigger-set position. The cam disk is shown in one of the depth setting positions and the spring is in a compressed state;

FIG. 10 shows an enlarged side cross-section view of the embodiment shown in FIG. 1. The device is shown with lancet holding member, trigger, spring and cam disk removed to expose an inside of the front and rear cover members, which are connected to one another;

FIG. 11 shows another enlarged side cross-section view of the embodiment shown in FIG. 1. The device is again shown with lancet holding member, trigger, spring and cam disk removed to expose an inside of the front and rear cover members. The front and rear covers are also separated from each other;

FIG. 12A shows an enlarged side view, in partial cross-section, of the holding member used in the embodiment shown in FIG. 1;

FIG. 12B shows a top view of the holding member shown in FIG. 12A;

FIG. 32 shows the trigger in the armed position and FIG. 33 shows the trigger being prevented from again assuming the armed position after being triggered;

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-15 show a first non-limiting embodiment of a single-use and/or disposable lancet device LD. Lancet device LD has a lancet body made up of an upper or front body portion 10 and a lower or rear body portion 20. These parts 10 and 20 are connected to each other, e.g., using adhesives and/or fasteners and/or welding and/or snap-together holding mechanisms (not shown), when the lancet device is initially assembled. A holding member 30 is movably disposed within the body parts 10, 20 (see FIGS. 3-5). Although not shown, a front end cover can also be removably connected or attached to a front portion of the body parts 10, 20 as in the embodiment described in copending U.S. patent application Ser. No. 10/441,065 filed on May 20, 2003, the entire disclosure of which is hereby expressly incorporated by reference in its entirety. Although not shown, the instant embodiment can also utilize a lancet holding member which accommodates a removable lancet tip of the type described in U.S. application Ser. No. 10/441,065. By removing the front end cover in such an arrangement, one can gain access to the lancet. In this way, the lancet can be installed prior to the single-use device being used.

As in many lancet devices, the lancet device defines a plane P which is configured to contact (i.e., be positioned against) a user's skin. However, unlike known lancet devices, the instant embodiment may utilize an inwardly curved surface plane P beyond which the lancet need can extend. Of course, the invention also contemplates using a planar front skin engaging surface, e.g., of the type described in U.S. Pat. No. 6,258,112, the disclosure of which is hereby expressly incorporated by reference in its entirety. The lancet needle LN itself can be conventional and be of the type disclosed in U.S. Pat. No. 6,258,112. Alternatively, it can be of the type which is replaceable, as is the case in many prior art lancet devices.

Figure 1:
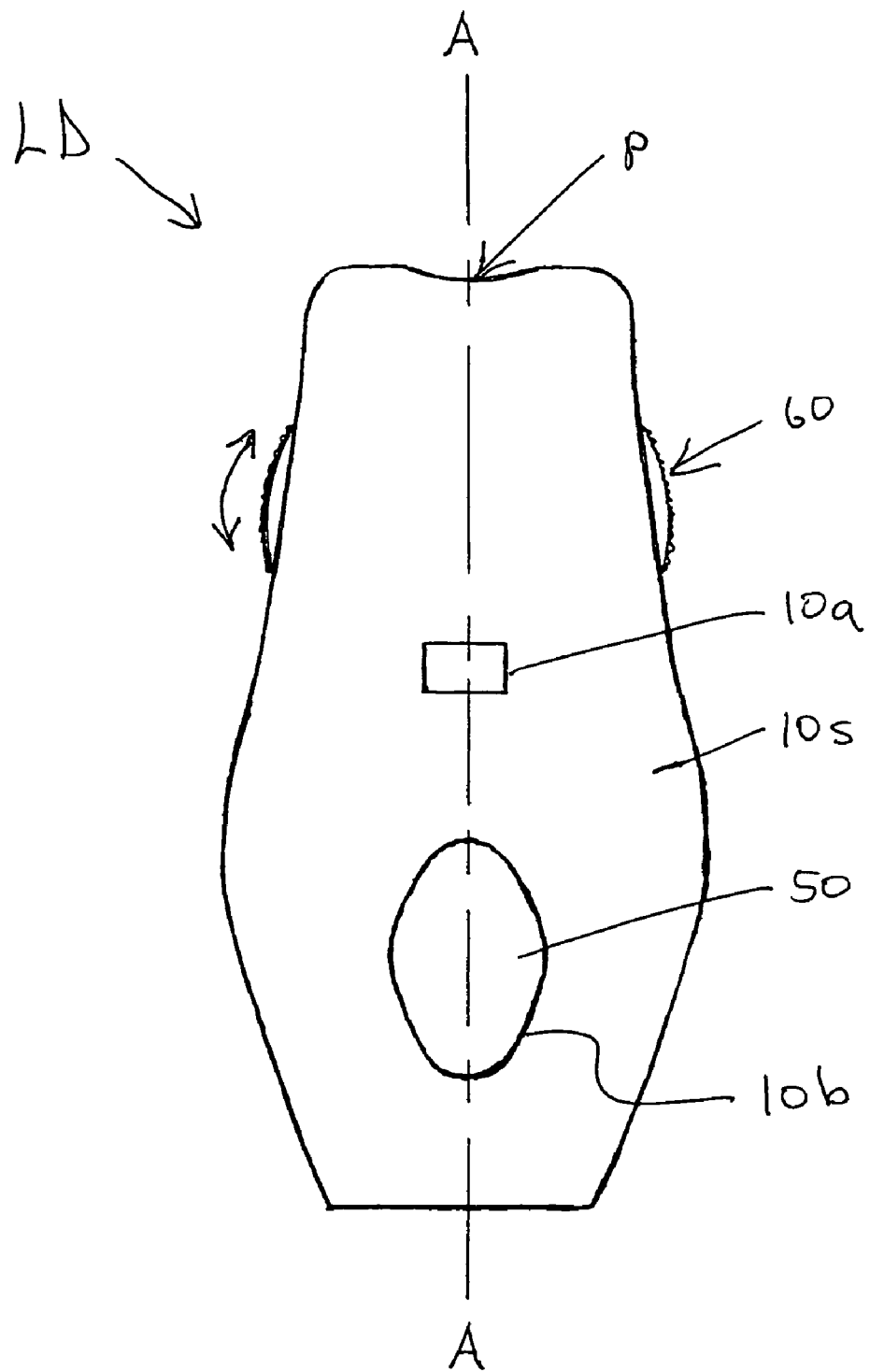
FIG. 1 shows a front side view of one embodiment of the single-use lancet device. The device is shown in the loaded (trigger set) position.
Figure 2:
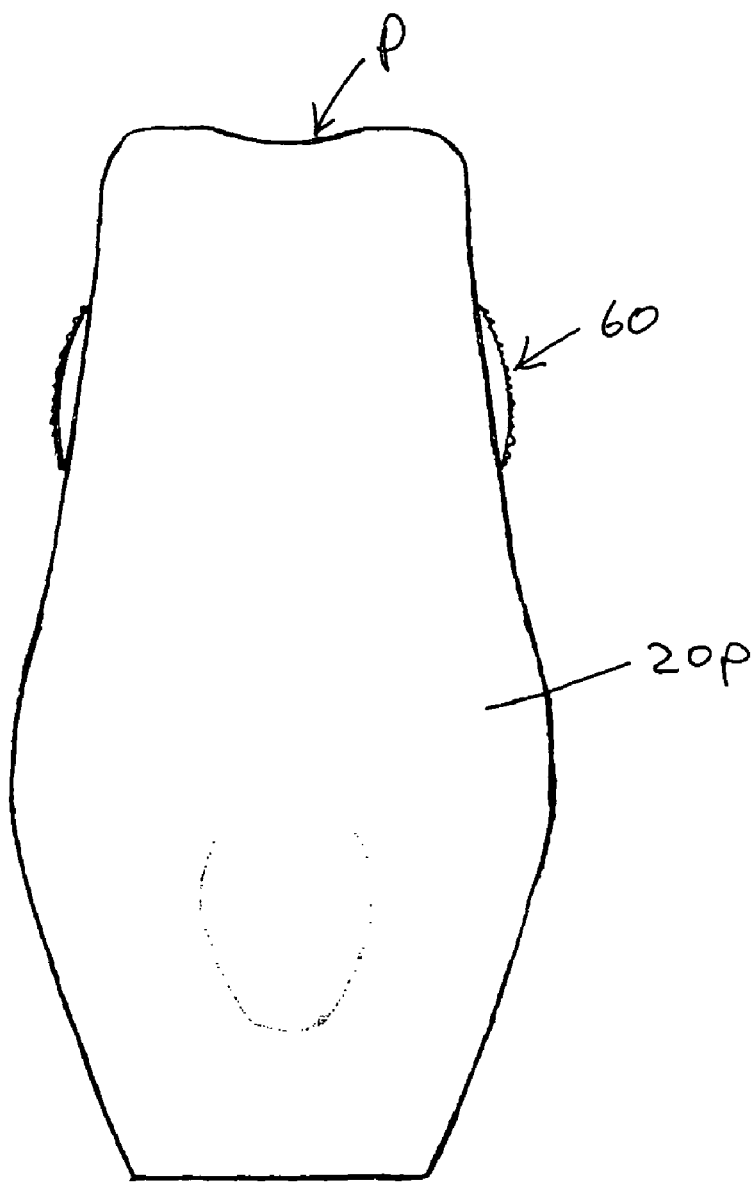
FIG. 2 shows a rear side view of the embodiment of FIG. 1.

As can be seen in FIGS. 1 and 2, the lancet body is preferably ergonomically shaped. In this regard, the lancet body can have an elongated clam-shape or pear shape. Of course, the invention contemplates other shapes provided that they result in a relatively inexpensive design and/or which is economical to produce. As explained above, the front end of the lancet device includes an inwardly curved skin engaging plane P which is defined by outer front inwardly curved surfaces of both cover parts 10, 20. A lancet opening LO is arranged on the plane and serves to allow the lancet needle LN to penetrate beyond the plane P (see FIG. 4). A trigger 50 is movably mounted to the lancet body. In the instant embodiment, the trigger 50 is oval-shaped or egg-shaped for reasons of aesthetic design. However, the invention contemplates other shapes for the trigger 50 such as, e.g., circular, triangular, square, polygonal, etc. In the instant embodiment, the trigger 50 is generally centrally mounted to a rear area of the front cover 10. However, the invention contemplates other locations and/or positions for the trigger 50. The trigger 50 is seated in a trigger opening 10b formed in the front cover 10. The trigger 50 has a finger engaging (e.g. push button) portion 50a (see FIG. 13A) that can be pushed into the lancet body. The trigger 50 also functions, in combination with its attachment to the front cover 10, as a spring in that it is capable of deflecting inwards (see FIG. 15) when force is applied to the finger engaging portion 50a, and is also capable of returning to a pre-deflection position (see FIG. 9).

The lancet body preferably also includes a viewing opening 10a. The opening or window 10a is formed in the front cover 10 and is arranged in a convenient area which allows the user to see indicia (see e.g., FIG. 8A) on the cam disk 60. As the user rotates the cam disk 60, the indicia 60j are viewed in the opening 10a. Thus, the opening 10a serves the function of a window which allows the user to note which cam surface setting position is set by the cam disk 60. The opening 10, of course, can have any desired shape or configuration and can be located at any desired location provided that the user is able to discern the desired setting position of the cam disk 60. The lancet body also includes two side openings 10c formed in the side walls 10d and 10e of the front cover 10 (see FIG. 10). These side openings 10c allow generally oppositely facing portions of the cam disk 60 (see FIG. 1) to protrude through the two sides the lancet body. In this way, a user can cause clockwise and/or counter-clockwise movement (see arrows in FIG. 1) of the cam disk 60 by rotating the protruding portions of the cam disk 60.

Figure 3:
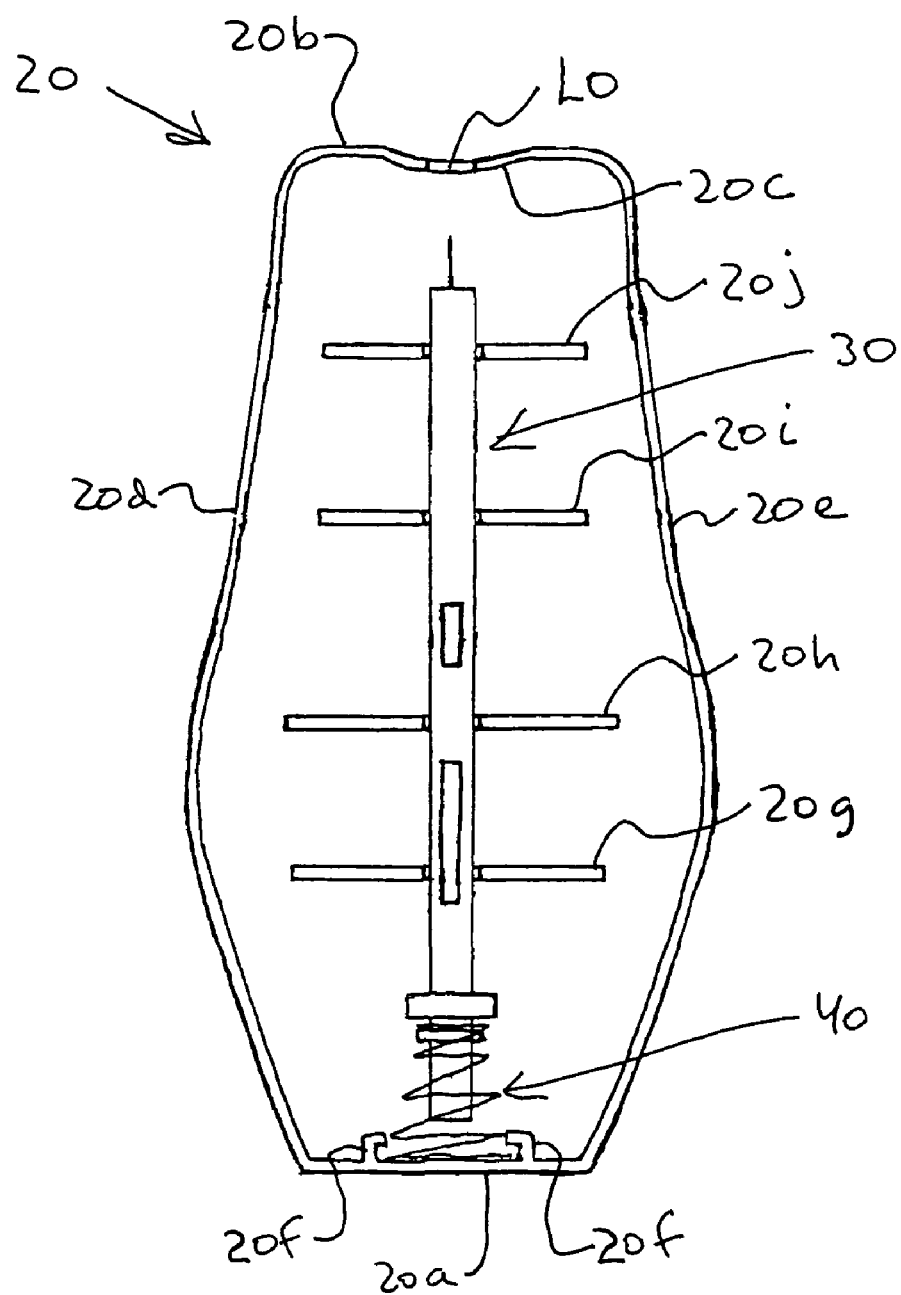
FIG. 3 shows a front side view of the embodiment shown in FIG. 1. The device is shown with the front cover removed thereby exposing the inside of the rear cover. The lancet holding member is in a loaded (retracted) position and the spring is compressed.

As can be seen in FIG. 3, the holding member 30 preferably has a spring 40 mounted thereto. In this regard, the spring 40, which can be made of spring steel and which can have the form of a tapered helical coil spring, is arranged in a rear area of the holding member 30. This spring 40 causes (and/or biases) the holding member 30 to move towards an extended position once a trigger 50 is activated (see FIG. 15). As discussed above, the trigger 50 includes a portion that is arranged within the body and is mounted to the upper body part 10. The spring 40 has a smaller diameter end 40a which is secured to the holding member 30 and a larger diameter end 40b which is secured to the lancet body (see also FIG. 14). In particular, the smaller end 40a is axially retained between a small diameter shoulder 30g and a large diameter shoulder 30f (see FIGS. 12A and 12B). The larger end 40b is axially retained and/or connected to projecting flanges 10f and 20f of the lancet body. The spring 40 also causes (and/or biases) the holding member 30 to move back towards an intermediate or normal position (see FIG. 5) after the lancet needle reaches the extended position (see FIG. 4). In this way, the lancet needle (and holding member 30) is automatically retracted after puncturing the skin of a user. In the embodiment shown in FIGS. 1-15, the lancet device is pre-loaded so that a user need only press the trigger 50 to use it. Once triggered, however, the user will be unable to use the device again owing to the fact that this embodiment contains no mechanism for forcing or moving the holding member 30 from the position shown in FIG. 5 to the armed or retracted position shown in FIGS. 3 and 9. Moreover, because the spring 40 maintains the holding member 30 in the position shown in FIG. 5, the lancet needle LN is kept safely within the lancet body. By way of non-limiting example, the armed position of the holding member 30 shown in FIGS. 3 and 9 can be set when the lancet device is manufactured and/or assembled by compressing the spring 40 to a certain extent until the stop surface 30e of the deflecting member 30d engages with the stop surface 10g of the stop projection 10h.

Figure 4:
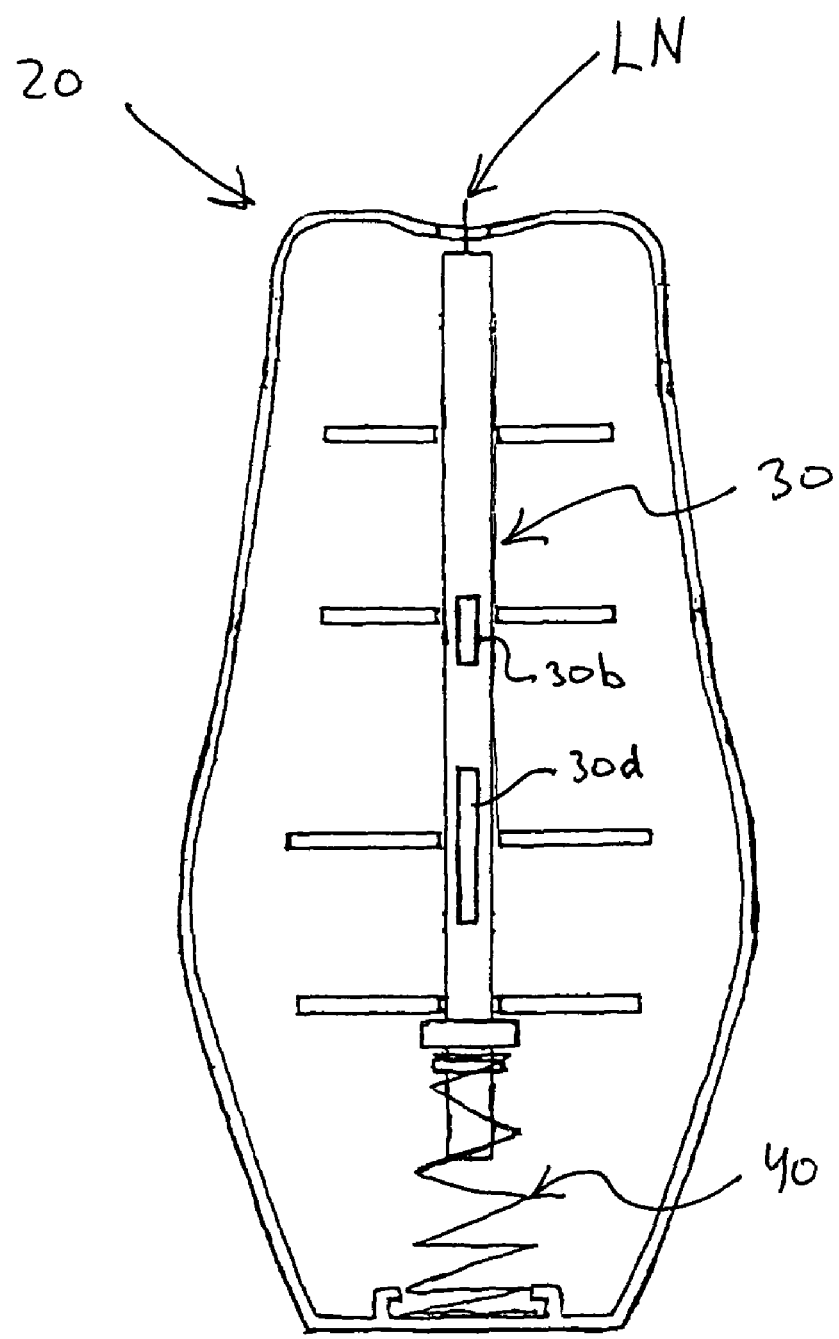
FIG. 4 shows another front side view of the embodiment shown in FIG. 1. The device is again shown with the front cover removed thereby exposing the inside of the rear cover. The lancet holding member is in an extended depth set position and the spring is expanded.
Figure 5:
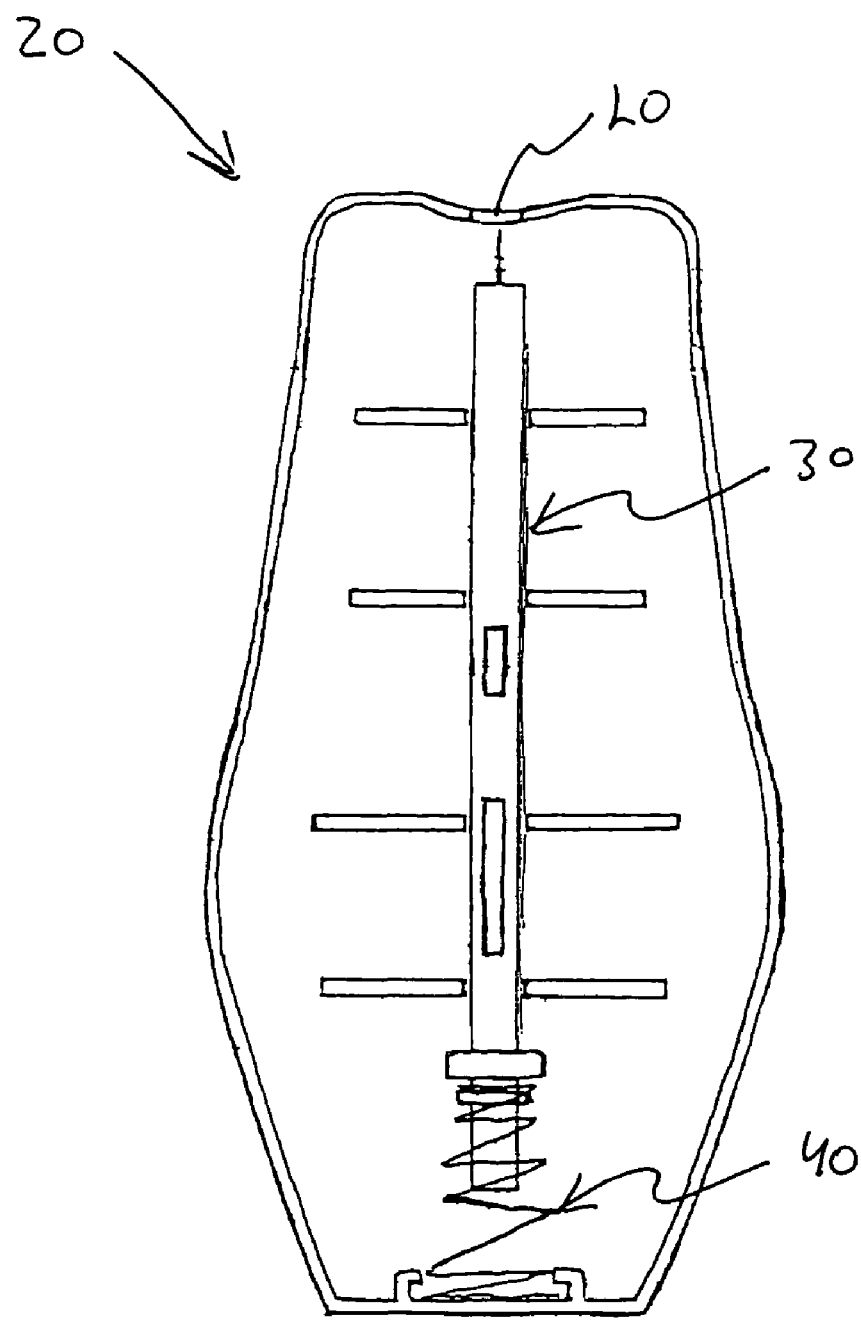
FIG. 5 shows still another front side view of the embodiment shown in FIG. 1. The device again is shown with the front cover removed thereby exposing the inside of the rear cover. The lancet holding member is in an original and/or a partially retracted position and the spring is in a normal and/or intermediate state in which it is neither compressed nor expanded.

FIGS. 3-5 show views of the lower body part 20 and the various positions of the holding member 30. The lower body part 20 can preferably be made as one-piece structure by e.g., injection molding. In this regard, it is preferably made of a plastic or synthetic resin such as, e.g., ABS plastic. The lower body part 20 may also be made of ABS—Metallic Silver and have a finish designated as SPI-A2. Of course, other materials and/or finishes may be utilized, without leaving the scope of the invention. Additionally, the lower body part 20 may have an overall length that is between approximately 2.5" and approximately 4". Although undesirable for reasons of cost, the lower body part 20 may even be made of a plurality of sections of parts which are joined together to form the complete lower body part 20, without leaving the scope of the invention.

The lower body part 20 preferably has a front straight wall 20a which includes a circular and/or curved center wall section 20c. The lower body part 20 also preferably has a curved bottom surface 20p (see FIG. 2). This surface 20p extends from the rear wall 20a to the front wall 20b and may have a large radius of curvature on the order to two or more feet and/or it may be essentially straight. The lower body part 20 additionally preferably includes four plate-like projections 20g-20j (see also FIG. 10) which are generally centrally disposed relative to side walls 20d and 20e. The purpose of these projections 20g-20j is to help guide the holding member 30 along a generally linear path. In this regard, the projections 20g and 20h are spaced apart by a distance which is generally similar to a distance separating projections 20i and 20j. Two L-shaped projecting walls 20f extend inwardly from the wall 20a of the lower body 20. These walls 20f retain end 40b of spring 40. In order to allow the holding member 30 move freely (without also rotating) within the lancet device and without being obstructed by the ribs 20g-20j, circular, square or rectangular shaped recesses 20k-20m (e.g., corresponding to the cross-sectional shape of the holding member 30) are formed in the center of the ribs 20g-20j. These recesses 20k-20m (see FIG. 10) are preferably slightly larger than the holding member 30 to allow it to move freely within the lancet device LD.

The lower body part 20 also preferably includes circular or curved indented side wall portions 20d and 20e. These curved walls 20d and 20e may have a radius of between approximately 1" and approximately 2". As described previously, these walls 20d and 20e allow a user to access the cam disk 60. That way, the user can use one or more fingers to rotate the cam disk 60 from either side 20d and/or side 20e. As seen in FIG. 3, the lower portion of sides 20d and 20e which extends to the rear wall 20a can be curved outwardly (i.e., convex) and have a radius of approximately 2".

Figure 6:
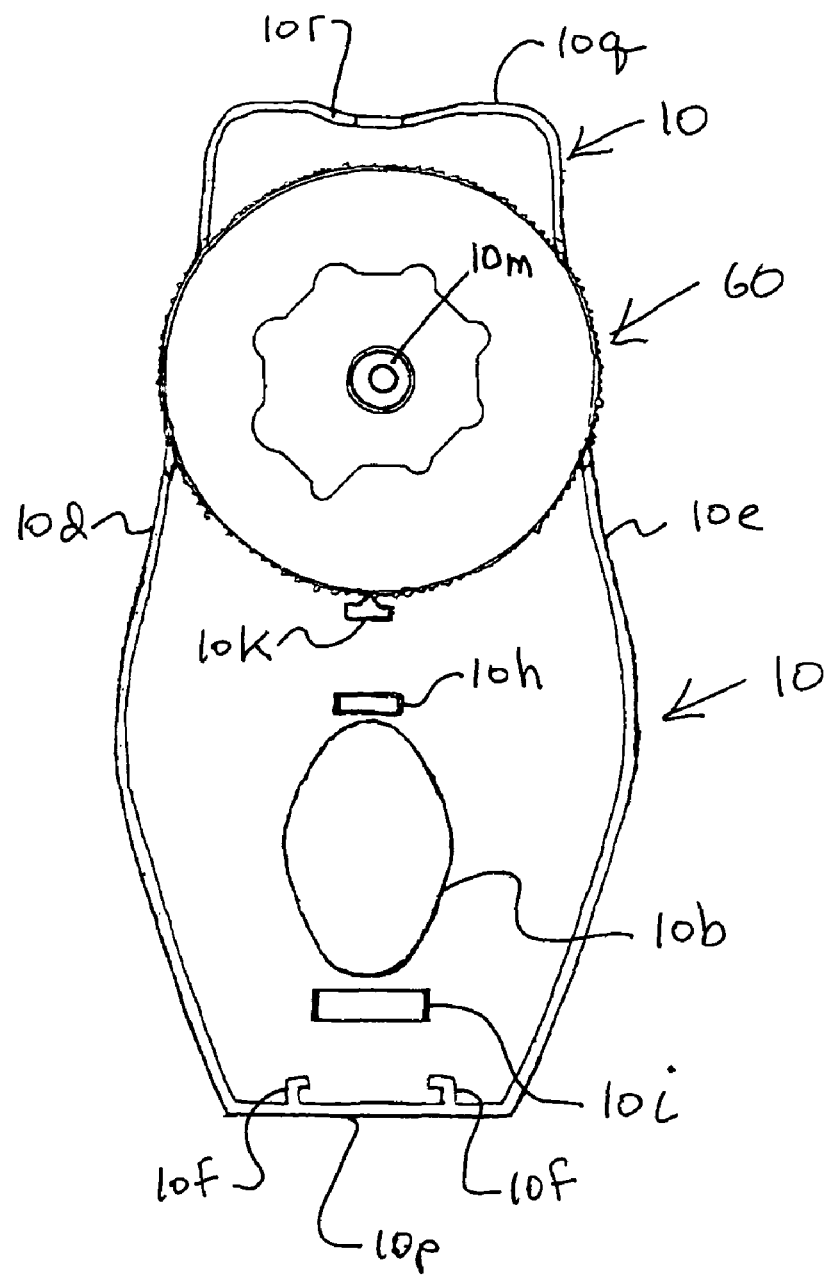
FIG. 6 shows a rear side view of the embodiment shown in FIG. 1. The device is shown with the rear cover removed thereby exposing the inside of the front cover. The trigger has been removed and the cam disk is shown rotatably mounted to the front cover.
Figure 7:
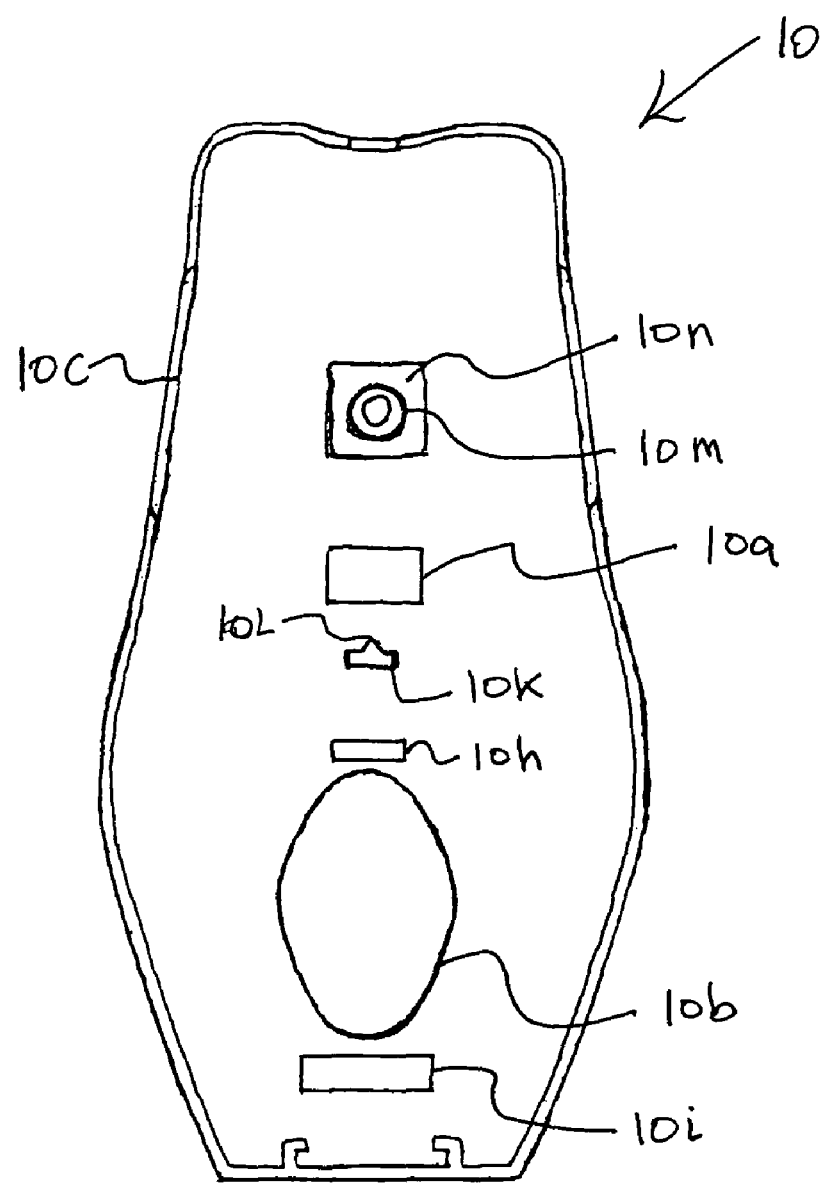
FIG. 7 shows another rear side view of the embodiment shown in FIG. 1. The device is again shown with the rear cover removed thereby exposing the inside of the front cover. Both the trigger and the cam disk have been removed from the front cover.

FIGS. 6 and 7 show inside views of the upper body part 10 and cam disk 60. The upper body part 10 can preferably be made as one-piece structure by e.g., injection molding. In this regard, it is preferably made of a plastic or synthetic resin such as, e.g., ABS plastic. The upper body part 10 may also be made of ABS—Metallic Silver and have a finish designated as SPI-A2. Of course, other materials and/or finishes may be utilized, without leaving the scope of the invention. Additionally, the upper body part 10 may have an overall length that is between approximately 2.5" and approximately 3" (i.e., between walls 10p and 10q). Although undesirable for economic reasons, the upper body part 10 may even be made of a plurality of sections of parts which are joined together to form the complete upper body part 10, without leaving the scope of the invention.

As was the case with the lower body part 20, the upper body part 10 preferably has a front straight wall 10q which includes a circular and/or inwardly curved wall 10r. The radius of this wall 10r should correspond to that of wall 20c. Arranged on the front side wall 10s is an oval or egg-shaped through opening 10b. This opening 10b is sized and configured to receive the push button portion 50a of the trigger 50 (see FIG. 13A). Of course, the opening 10b can have any desired size, shape or configuration provided it allows a user access to the trigger 50 and provided that it generally corresponds to the size, shape and configuration of the trigger 50. The opening 10b is formed in front wall between an inwardly projecting shoulder 10h and a projecting bearing flange 10i. As was described previously, this shoulder 10h is sized, shaped and/or configured to be engaged by the deflecting member 30d (see FIG. 9). In this regard, the projection 10h has a straight contact stop surface 10g that is generally parallel to walls 10p and 10q. The projection 10h can also be oriented at a slight angle in order to ensure that the deflecting member 30d easily disengages from the projection 10h upon actuation of the trigger 50. As will be described later on with regard to FIG. 9, the generally straight contact surface 10g of projection shoulder 10h is configured to be engaged by surface 30e of deflecting member 30d. Moreover, an opening 10j of the projecting flange 10i is configured to receive therein a rear projection 50b of the trigger 50 (see FIGS. 9 and 10).

The upper body part 10 additionally preferably includes a plate-like projection 10k which is generally centrally disposed relative to sides 10d and 10e. The purpose of this projection 10k is to temporarily lock the cam disk 60 in a desired rotational position. The projection 10k includes a centrally disposed tooth 10l which engages the circumferential teeth or ribs 60h of the cam disk 60. When the cam disk 60 is rotated, the engagement between the tooth 10l and ribs 60h of the cam disk 60 create a clicking sound as the projection 10k deflects towards and away from the cam disk 60 during rotation. Once a desired rotational position of the cam disk 60 is reached (indicated by the desired indicia 60i being visible in the opening 10a), engagement between the tooth 10l and one of the numerous circumferential notches 60h of the cam disk 60 prevents the cam disk 60 from rotating out of a depth set position. The L-shaped projection 10i also extends inwardly from the front wall 10s of the upper body part 10. This projection 10i forms a bearing/elastic pivot system for the trigger 50 (see FIGS. 9 and 15). As will be described later on with regard to FIG. 15, the projection 10i and a recess 10j pivotally support a rear projecting portion 50b of the trigger 50.

Figure 24:
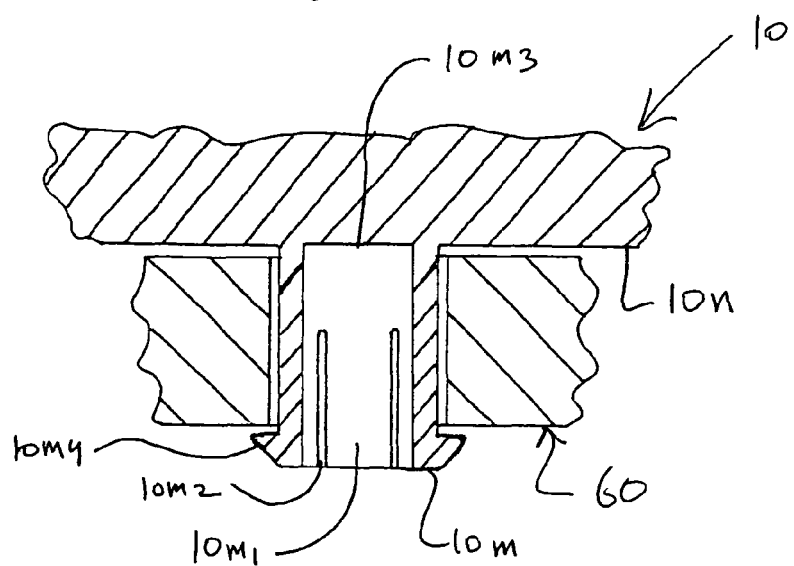
FIG. 24 shows an enlarged partial cross-section view of one way in which the cam disk used in the embodiments shown in FIGS. 1-19 can be rotatably mounted to the front cover member.
Figure 28:
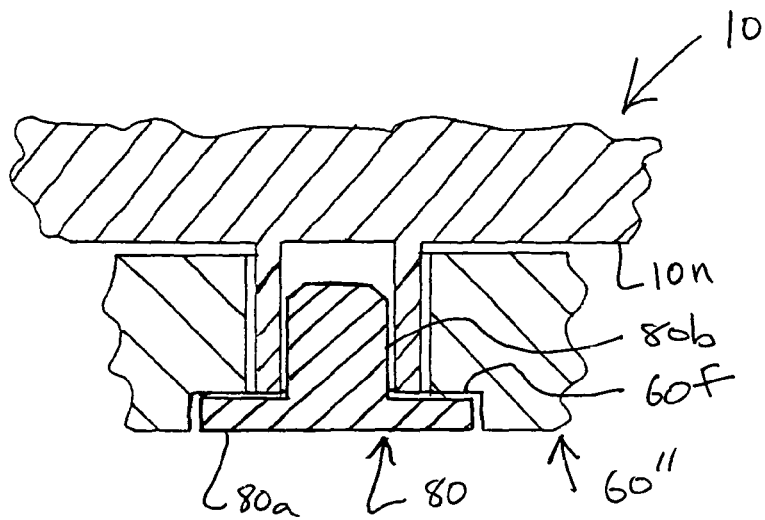
FIG. 28 shows an enlarged partial cross-section view of another way in which the cam disk of the type used in the embodiments shown in FIGS. 1-19 can be rotatably mounted to the front cover member. This attachment system utilizes a fastener-shaped plug whose head portion is recessed into a counterbore of the cam disk.
Figure 29:
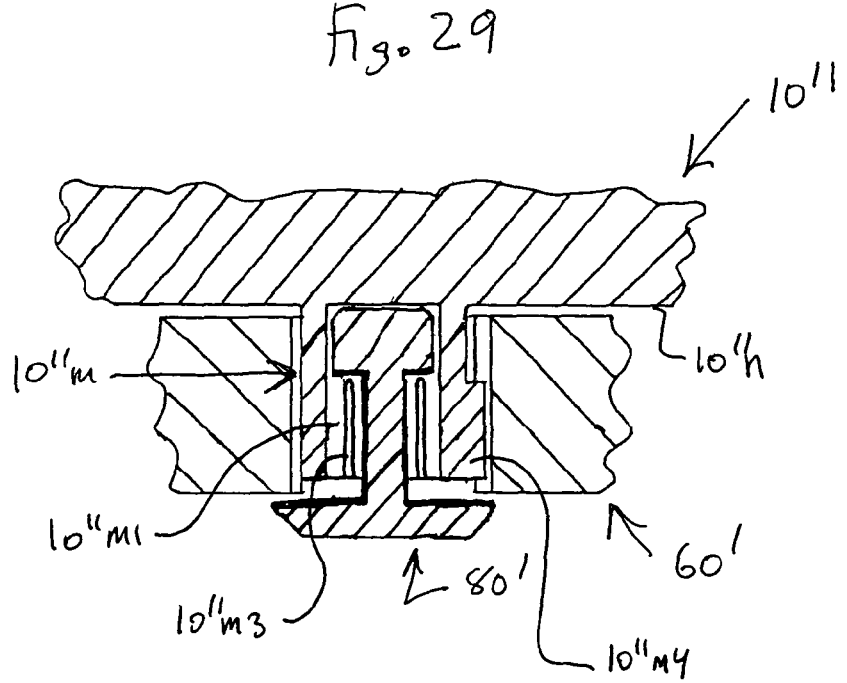
FIG. 29 shows an enlarged partial cross-section view of another way in which the cam disk used in the embodiments shown in FIGS. 20-23 can be rotatably mounted to the front cover member. This attachment system utilizes a fastener-shaped plug.

As is seen in FIGS. 6 and 7, the upper body part 10 further includes a circular bearing journal 10m that is generally centrally disposed relative to sides 10d and 10e. The purpose of this journal 10m is to provide a rotatable mounting for the cam disk 60 (see also FIG. 9). The journal 10m has a generally cylindrical outer surface on which an inner circular opening 60b (with a small clearance) of cam disk 60 rotates. The journal 10m also may also have an inner recess (see FIGS. 24 and 28) that includes a cylindrical portion 10m1 and a bottom end 10m3 by way of non-limiting example. The cylindrical portion 10m1 of the recess can also be sized to receive (i.e., with frictional engagement) a slightly tapered projecting portion 80b of a retaining member 80 (see FIG. 28). A square-shaped (or any other desired shape) bearing surface 10n is arranged at a bottom end of the journal 10m. This surface 10n serves to axially retain surface 60g of the cam disk 60. On the other hand, once the retaining member 80 is assembled to journal 10m so as to trap the cam disk 60/60" (see e.g., FIG. 28), the cam disk 60/60" becomes axially retained between surface 10n and part 80a. The connection system shown in FIG. 24 is preferably utilized for retaining the cam disk 60 because it results in a lower cost device (owing to the fact that the journal 10m is integrally formed with the upper housing part 10) and because it allows the cam disk 60 to be axially retained between surface 10n and the radially projecting portion 10m4 of projection 10n. Of course, the distance between these axially retaining surfaces is made to be slightly greater than a thickness (measured between surfaces 60d and 60g) of the cam disk 60 so that the cam disk 60 can rotate somewhat freely, i.e., with reduced friction. This is also ensured if there is a slightly lose fit between the outer cylindrical surface of journal 10m and the inner diameter 60b of cam disk 60. The bearing surface 10n also projects slightly from an inner surface of wall 10s of upper body part 10 (see FIG. 9).

As explained above, the lancet device LD utilizes a cam disk 60 to adjust the penetration depth of the lancet needle.

The cam disk 60 is preferably mounted to the upper body part 10 and is preferably at least partially rotatable in each of two directions. Of course, the cam disk 60 can be mounted within the body in any desired manner provided that it functions properly. The invention also contemplates allowing the cam disk 60 to only rotate in one direction, i.e., either clockwise or counterclockwise. As noted above, to ensure that the cam disk 60 is axially retained to body part 10, yet allowed to rotate with respect to upper body part 10, a retaining system may be utilized (See, e.g., the retaining systems of FIGS. 24-29). As will be more fully described in detail later on, the cam disk 60 has a plurality of cam surfaces 60e1-60e8 (see FIG. 8C) which are configured to be engaged by a stop projection 30b (in particular stop surface 30c of stop projection 30b) that is formed on or coupled to the holding member 30.

The operation of the device will now be explained. FIG. 3 shows the lancet device LD with the lancet member 30 in the loaded position, i.e., ready to move to an extended position when the trigger 50 is pressed. The holding member 30 retains the loaded position of FIG. 3 as a result of engagement between a deflecting member 30d and a shoulder 10h of the upper body part 10. On the other hand, FIG. 4 shows what happens when the trigger 50 is pressed, i.e., the trigger 50 is caused to be deflected inwardly (see also FIG. 15). That is, the holding member 30 is released from the loaded position of FIGS. 3 and 9, and is caused to move towards plane P. This occurs because the trigger 50 causes the deflecting member 30c to disengage from the shoulder 10h of the upper body part 10. As discussed above, this movement is caused by the expansion (in the direction of a the axis of the holding member 30) of the spring 40. The holding member 30 continues to move towards the plane P until the stop projection 30b contacts or engages one of the stop surfaces 60e1-60e8 of the cam disk 60. Once the trigger 50 is released (once a user stops pressing on the trigger 50), the trigger 50 preferably moves back (e.g., automatically) to an un-deflected state shown in FIG. 9. However, unlike known prior art devices, the lancet device contains no mechanism for reloading and/or moving the holding member 30 back into the position shown in FIG. 9, i.e., the lancet device LD cannot then be placed back into the position shown in FIG. 9 because the device contains no mechanism for placing the deflecting member 30d back into engagement with the shoulder 10h. Indeed, the spring 40, by being coupled at both ends to the body and the holding member 30, and by ensuring that the holding member 30 assumes an original position shown in FIG. 5, ensures that the holding member 30 cannot be re-armed, and ensures that the holding member 30 (along with the lancet needle) is safely retained within the body.

Figure 15:
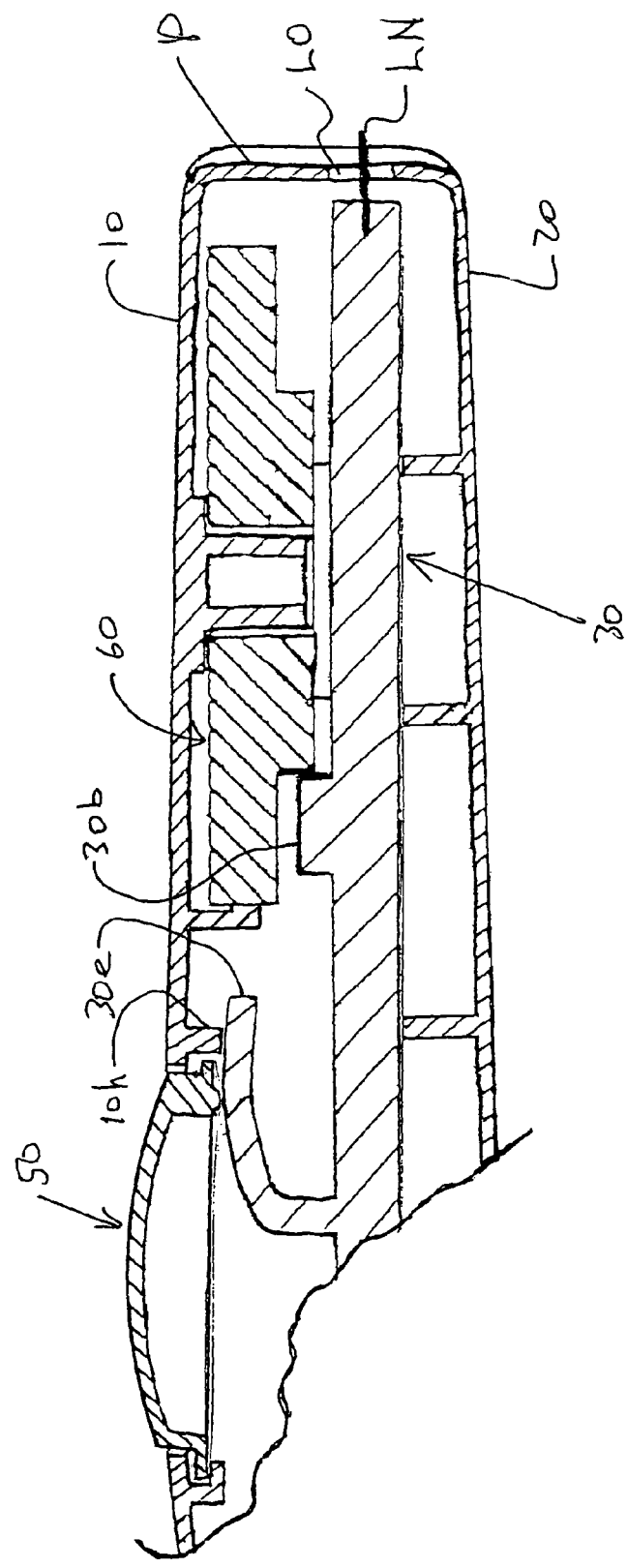
FIG. 15 shows an enlarged partial side cross-section view of the embodiment shown in FIG. 1. The device is shown with lancet holding member in the extended position after being caused to move by the trigger and the spring. This depth penetration position is characterized by contact between the stop surface of the holding member and one of the cam surfaces of the cam disk, and with the lancet needle projecting though the lancet opening and beyond the plane.
Figure 16:
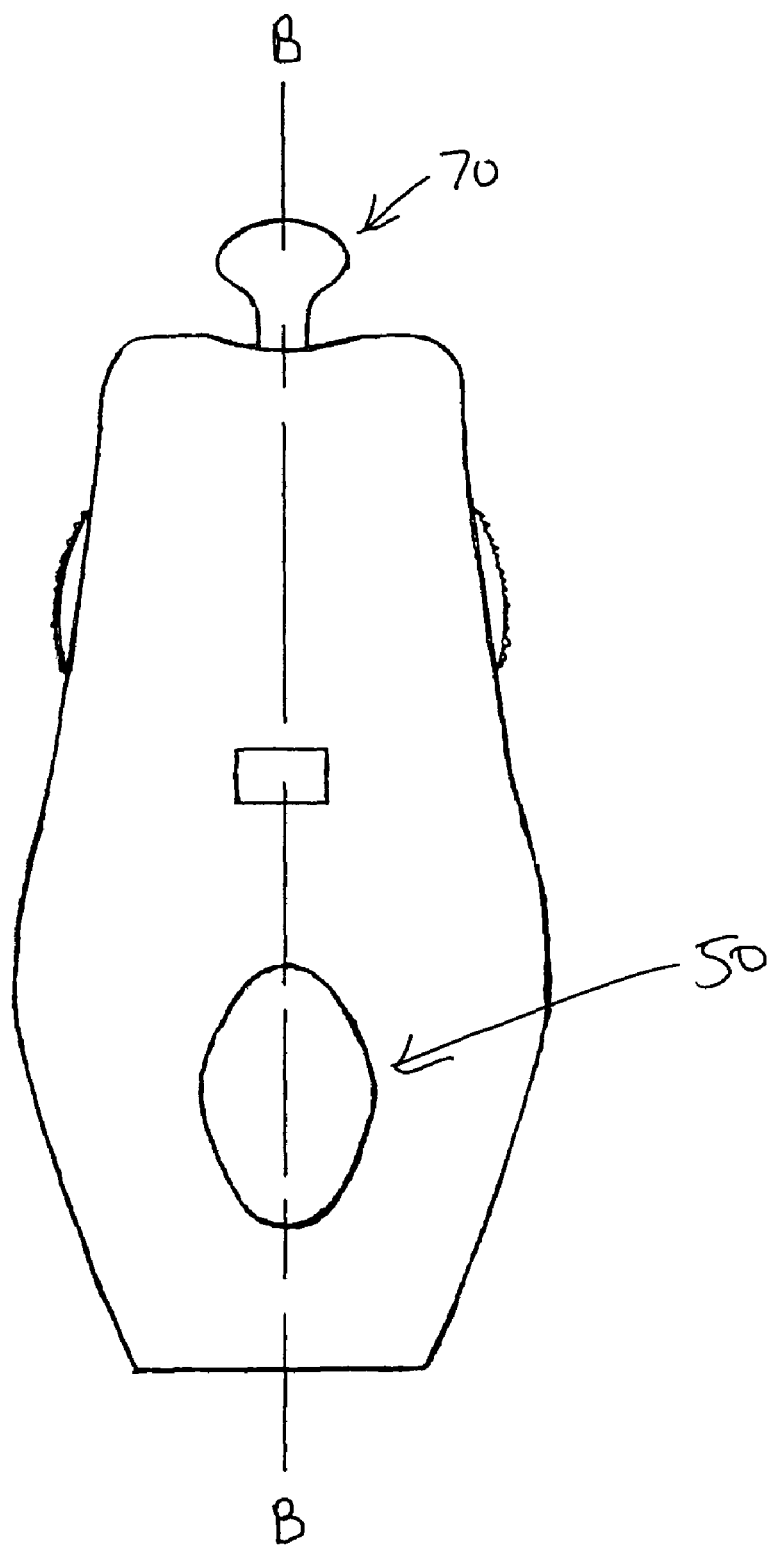
FIG. 16 shows a front side view of another embodiment of the single-use lancet device. The device is shown in a normal or intermediate position prior to being loaded or armed.
Figure 17:
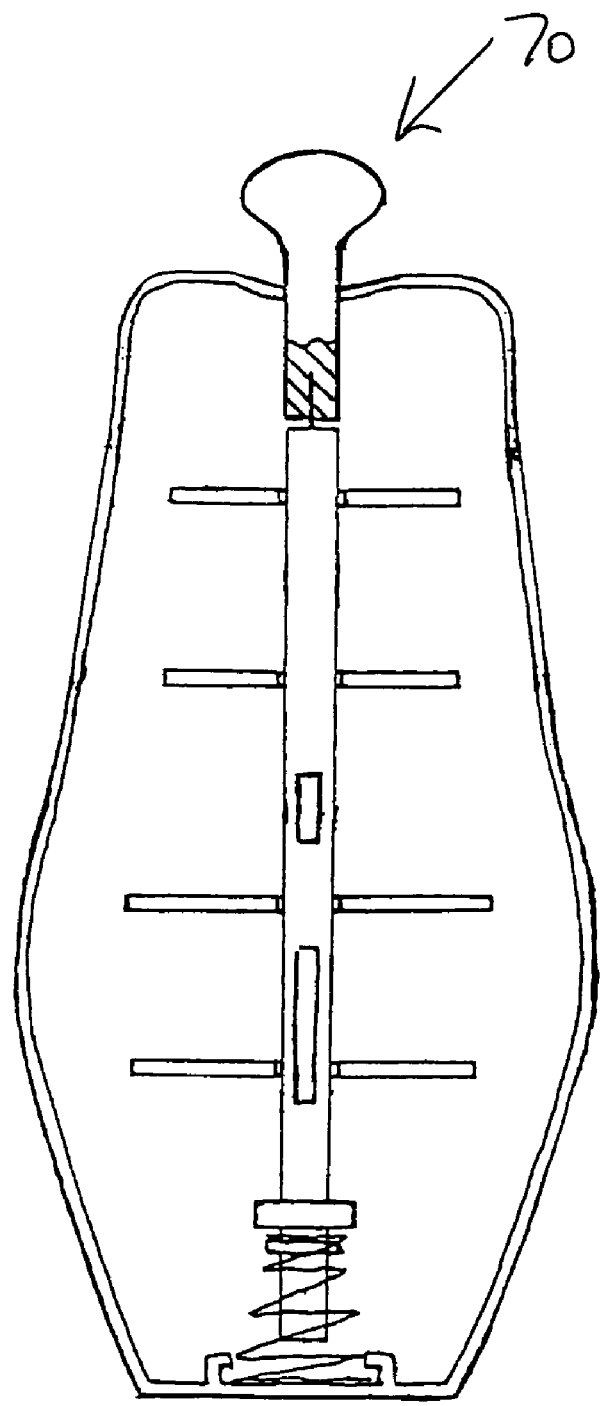
FIG. 17 shows a front side view of the embodiment shown in FIG. 16. The device is shown with the front cover removed thereby exposing the inside of the rear cover. The lancet holding member and needle are in the normal position and a tab is shown covering the tip of the lancet needle.
Figure 18:
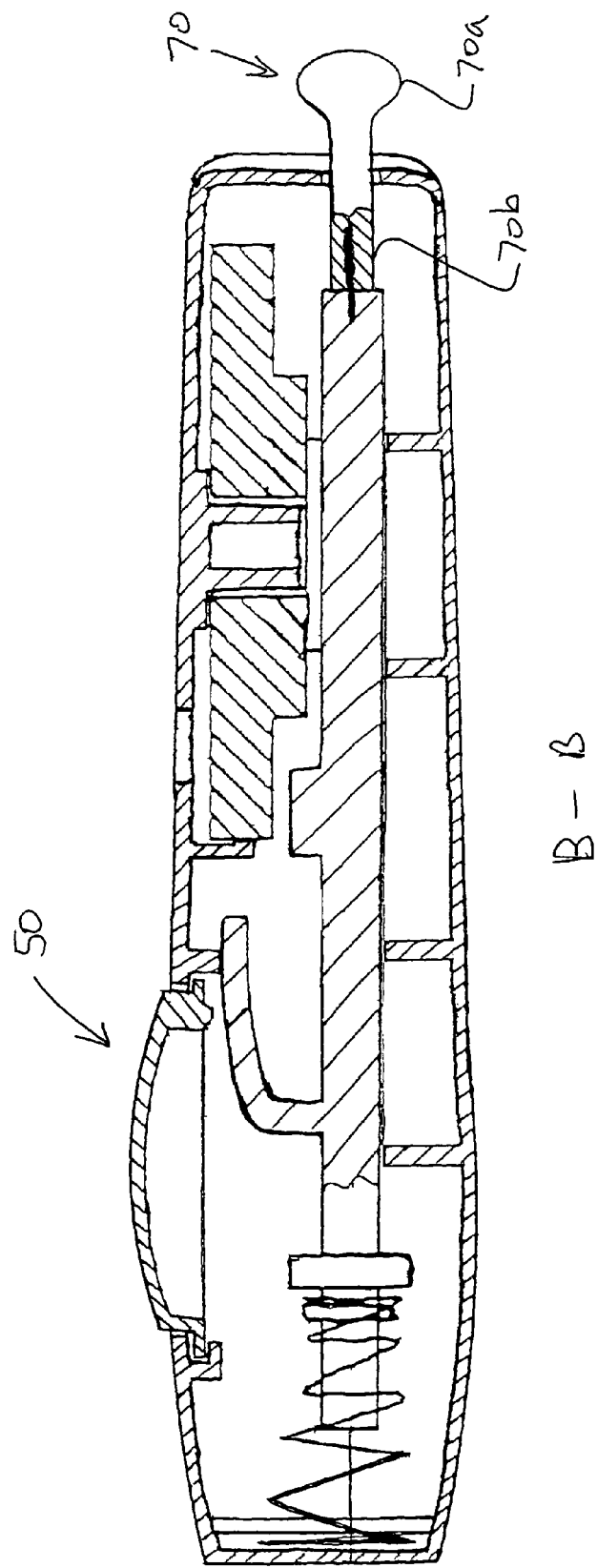
FIG. 18 shows an enlarged side cross-section view of the embodiment shown in FIG. 16. The device is shown with the lancet holding member in an original and/or intermediate and/or relaxed position.
Figure 19:
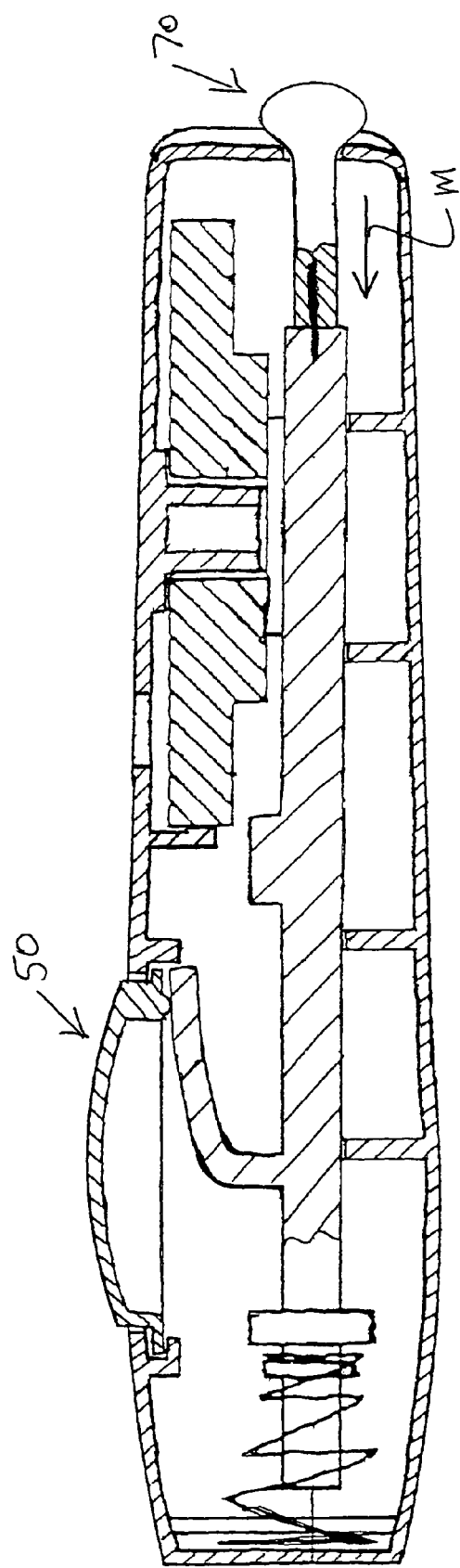
FIG. 19 shows another enlarged side cross-section view of the embodiment shown in FIG. 16. The device is shown with the tab having caused the lancet holding member to move to the armed and/or fully retracted and/or trigger-set position. The cam disk is shown in one of the depth setting positions and the spring is in a compressed state.

FIG. 4 shows the lancet device with the holding member 30 in one of the pre-set extended positions, i.e., in one of the extended positions that will cause a desired puncture depth in the skin of a user (not shown). The distance that the lancet needle projects past plane P is thus determined by rotating the cam disk 60 until the desired setting is reached. This setting, in turn, causes a particular stop surface (i.e., one of surfaces 60e1-60e8) to be placed in the path of the stop projection 30b. The various stop surfaces (e.g., 8 surfaces shown in FIGS. 8A-D) of the cam disk 60 thus determine how much the holding member 30 will move in the extended position relative to the plane P. In this regard, FIG. 15 shows contact between the stop projection 30b and one of the surfaces 60e1-60e8 of the cam disk 60. FIG. 15 also shows the needle tip projecting through the opening LO and past the plane P.

FIGS. 8A-D show top, bottom and side cross-section views of the cam disk 60. The cam disk 60 can preferably be made as one-piece structure by e.g., injection molding. In this regard, it is preferably made of a plastic or synthetic resin such as, e.g., ABS plastic. The cam disk 60 may also be made of ABS—Dark Blue and have a finish designated as MT-11040. Additionally, the cam disk 60 may have an overall diameter that is approximately 0.78". Of course, other materials and/or finishes and/or sizes may be utilized, without leaving the scope of the invention. Moreover, the cam disk 60 may even be made of a plurality of sections of parts which are joined together to form the complete cam disk 60, without leaving the scope of the invention.

Figure 8B:
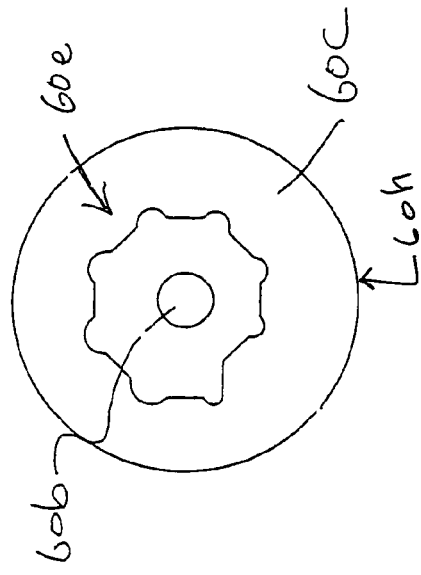
FIG. 8B shows a bottom view of the cam disk shown in FIG. 8A.
Figure 8D:
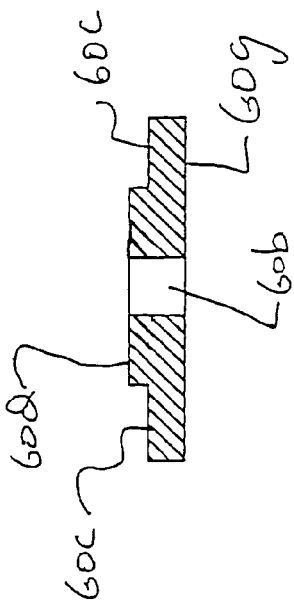
FIG. 8D shows a side cross-section view of the cam disk shown in FIG. 8B.
Figure 8A:
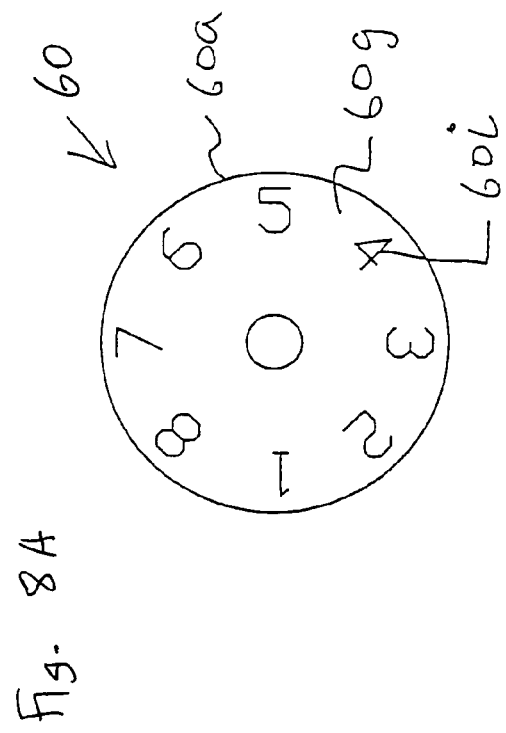
FIG. 8A shows a top view of the cam disk of the lancet device shown in FIG. 1.
Figure 8C:
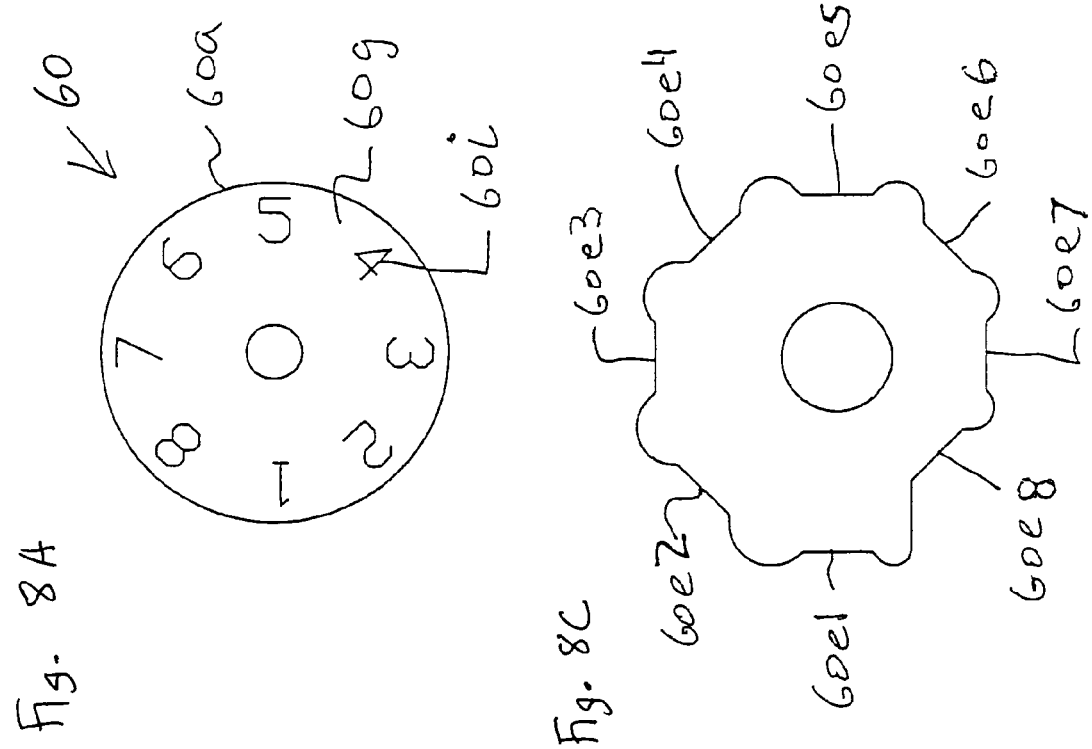
FIG. 8C shows an enlarged view of the cam portion of the cam disk shown in FIG. 8B.

The cam disk 60 preferably has a top surface 60g that includes indicia 60i which may be, e.g., numbers or letters. Of course, any desired indicia may be utilized. This indicia 60i can be, e.g., pad printed or silk screen raised numbers in, e.g., white ink. The height of the indicia can be approximately 0.09". A centrally disposed cylindrical opening 60b extends through the cam disk 60. The opening 60b may have a diameter of between approximately ⅛" and approximately ¼". As explained previously, the opening 60b is sized and configured to slide over cylindrical projection 10m of the upper body part 10. The cam disk 60 may also include an enlarged diameter opening that is defined by shoulder 60f (see e.g., FIG. 28). The diameter of the shoulder can be between approximately 0.25" and approximately 0.30". The purpose of this shoulder 60f is to receive head 80a of the retaining member 80 (see e.g., FIG. 28). As explained above, the cam disk 60 preferably includes a plurality of cam surfaces, e.g., eight cam surfaces 60e1-60e8, formed on a cam section 60e. As can be seen in FIG. 8C, the cam surfaces 60e1-60e8 are all spaced from a center axis of the cam disk 60 by different amounts. As was explained previously, these surfaces are configured to be contacted by stop surface 30c of the holding member 30. Thus, for example, when contact is made between stop surface 30c and surface 60e8, the lancet needle will penetrate to its deepest setting. On the other hand, when contact is made between stop surface 30c and surface 60e1, the lancet needle will penetrate to its shallowest setting. Of course, surfaces 60e2-60e7 will set the penetrating depth in between these extreme settings. Although, the cam disk 60 is configured with eight settings (designated by the number of cam surfaces and the indicia), the cam disk 60 can have any number of desired settings/cam surfaces that can range from two to as many as 20 or more, if desired.

In this regard, by way of non-limiting example, the distance between surface 60e8 and the center axis of cam disk 60 can be approximately 0.16", the distance between surface 60e7 and the axis of cam disk 60 can be approximately 0.169", the distance between surface 60e6 and the axis of cam disk 60 can be approximately 0.178", the distance between surface 60e5 and the axis of cam disk 60 can be approximately 0.187", the distance between surface 60e4 and the axis of cam disk 60 can be approximately 0.196", the distance between surface 60e3 and the axis of cam disk 60 can be approximately 0.205", the distance between surface 60e2 and the axis of cam disk 60 can be approximately 0.214", and the distance between surface 60e1 and the axis of cam disk 60 can be approximately 0.223". The surfaces 60e1-60e8 are separated by rounded projections which may have a radius of approximately 0.04". The width of the surfaces 60e1-60e8 can be approximately 0.08". The thickness of the cam section can be approximately 0.05" measured from surface 60c and 60d while the thickness of the indicia section can be approximately 0.08" measured from surface 60g and surface 60c. Finally, the cam disk 60 preferably includes a plurality of circumferential ribs and notches 60h which are sized and configured to engage with a tooth 10l of the projection 10k of the upper body part. These notches/ribs 60h ensure that the cam disk 60 is retained in a desired set-depth position indicated by the indicia. The notches/ribds 60h may also have the form of a knurl, a high-friction surface, or other desired texturing (e.g., projections and recesses) along its peripheral edge (not shown) in order to also facilitate gripping by the user and engagement by the tooth 10l.

FIG. 9 shows a cross-section view of the lancet device of FIGS. 1-8. In this regard, the holding member 30 is in the loaded/armed position shown in FIG. 3. As this figure illustrates, the upper body part 10 is coupled to the lower body part 20 and forms the lancet body. The spring 40, trigger 50, cam disk 60 and holding member 30 can be seen in their installed and/or assembled position. The spring 40 is preferably sized to slide onto a rear portion 30h of the holding member 30. More particularly, the spring 40 preferably has a large end 40b which is trapped and/or retained with the flanges 10f and 20f of the lancet body and a small end 40a which is trapped and/or retained between flanges 30g and 30f of the holding member 30. That is, the spring 40 is coupled to both the lancet body and the holding member 30. As a result, the spring 40 is caused to be compressed when the holding member 30 is moved back (i.e., to the left) to a retracted position relative to the lancet body. As discussed above, the spring 40 causes (and/or biases) the holding member 30 towards an extended position once a trigger 50 (see FIG. 15) is activated. Once triggered, the holding member 30 reaches a fully extended position and then assumes an intermediate position (see FIG. 5). The spring 40 also ensures that the holding member 30 cannot be moved back to a retracted position without causing the spring 40 to be compressed thereby.

As discussed above, the lancet device has a lancet body made up of an upper body portion 10 and a lower body portion 12. These parts 10 and 20 are connected to each other when the lancet device is initially assembled. In this regard, a seam line SL is preferably formed and/or provided between the bottom edges of the upper body part 10 and the top edges of the lower body part 20 (see FIGS. 10 and 11). In this way, one is prevented from gaining access to the lancet. The lancet can thus be retained safely within the lancet body so that it can be safely disposed of. As in many prior art lancet devices, the lancet device defines a plane P which is configured to contact (i.e., be positioned against) a user's skin.

FIGS. 10 and 11 shows a cross-section view of the lancet body used in the device of FIGS. 1-9. In this regard, the holding member 30, the spring 40, trigger 50, and cam disk 60 have been removed. As FIG. 10 illustrates, the upper body part 10 is coupled to the lower body part 20 and forms the lancet body. FIG. 11 illustrates how the separately formed upper and lower body parts 10 and 20 can be coupled to one another. As can be seen from these figures, the upper body part 10 includes a number of integrally formed features such as, a trigger opening 10b, an indicia window 10a, a trigger bearing support projection 10i, a stop projection 10h for retaining the deflecting member 30d, a cam disk engaging projection 10k whose tooth 10l engages with notches/ribs of the cam disk 60, a projecting journal 10m, bearing surface 10n, spring retaining projections 10f, side openings 10c, and approximately ½ of the circular lancet opening LO. The lower body part includes a number of integrally formed features such as, plate-like projections 20g-20j with recesses 20k-20n and approximately ½ of the circular lancet opening LO.

FIGS. 12A-B show side partial cross-section and top views of the holding member 30. The holding member 30 can preferably be made as one-piece structure by e.g., injection molding. In this regard, it is preferably made of a plastic or synthetic resin such as, e.g., Delrin plastic. The holding member 30 may also be made of Delrin—Natural and have a finish designated as SPI-C1. Of course, other materials and/or finishes may be utilized, without leaving the scope of the invention. Additionally, the holding member 30 may have an overall length that is between approximately 1" and 3". Moreover, the holding member 30 may even be made of a plurality of sections of parts which are joined together to form the complete holding member 30, without leaving the scope of the invention.

The holding member 30 preferably has a body portion 30a that is cylindrical (see e.g., FIG. 35) and which may have a diameter of between approximately ⅛" and approximately 0.25". The invention also contemplates other cross-sectional shapes for the holding member 30 such as square, oval, polygonal, etc. Indeed, a square cross-section may be preferred in order to ensure that holding member 30 does not rotate while moving within the lancet body (see e.g., FIG. 36). In this case, it is preferred that the recesses 20k-20n (see FIG. 10) be similarly sized and shaped to allow for such movement. The body 30a is sized and configured to securely retain and receive the lancet needle, which may be a conventional lancet needle. The holding member 30 also includes a rear cylindrical section 30h (or other shaped section) which may have a diameter of between approximately 1/8" and approximately 0.25". Cylindrical section 30h also includes a small circular projection flange 30g and a large circular projection flange 30f. The flanges 30g and 30f are sized and configured to retain the small end 40a of the spring 40 (see e.g., FIG. 14).

An integrally formed deflecting member 30d preferably extends from the cylindrical body or section 30a. This deflecting member 30d has a stop surface 30e which is configured to abut against stop surface 10g of shoulder 10h of the upper body part 10. A trigger engaging surface is arranged an upper portion of the deflecting member 30d. This surface is configured to be engaged by projection 50d of the trigger 50. As explained above, the deflecting member 30d is capable of deflecting inwards towards the holding member 30 when surface 50a is forced towards holding member 30. However, because the deflecting member 30d acts like a natural spring, the deflecting member 30d is capable of deflecting away from the holding member 30 when surface 30d is not being forced towards holding member 30. The length of the deflecting member 30d can be between approximately ¼ and approximately ½". The deflecting member 30d can also be spaced from the cylindrical section 30a by about 0.08". The deflecting member 30d may also has a width (measured in the direction of FIG. 12B) of between approximately 0.04" and 0.08". An integrally formed stop projection 30b also extends from the holding member 30. This projection 30b may have a length of between approximately ⅛" and approximately 0.20" and a width of approximately 0.05". The projection 30b also has a stop surface 30c. This stop surface 30c is adapted to engage and/or contact the various stop surfaces 60e1-60e8 of the cam disk 60. Thus, the stop surface 30c serves to adjust the depth of the lancet needle based upon the position of the cam disk 60, as was described above.

Figure 13A:
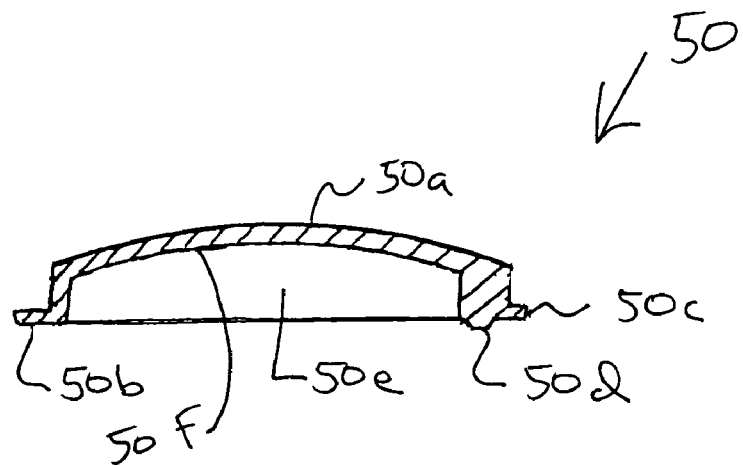
FIG. 13A shows an enlarged side cross-section view of the trigger used in the embodiment shown in FIG. 1.
Figure 13B:
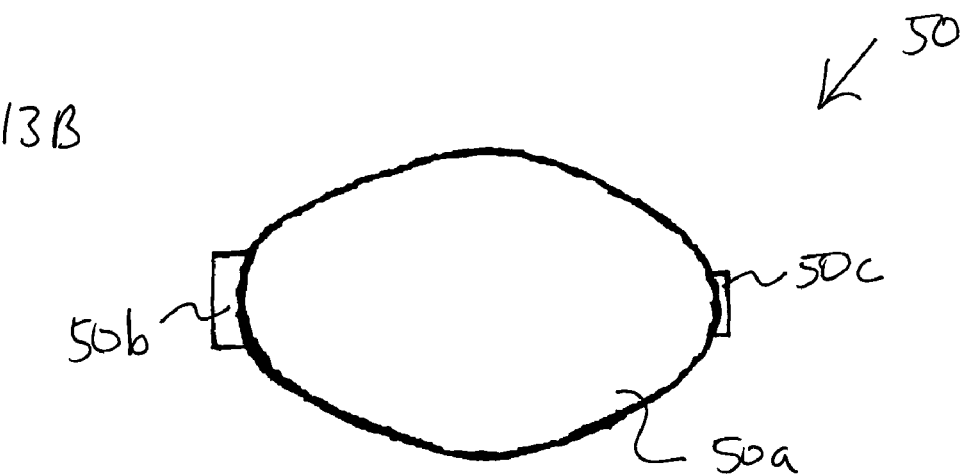
FIG. 13B shows a top view of the trigger shown in FIG. 13A.

FIGS. 13A-B show side cross-section and top views of the trigger 50. The trigger 50 can preferably be made as one-piece structure by e.g., injection molding. In this regard, it is preferably made of a plastic or synthetic resin such as, e.g., ABS plastic. The trigger 50 may also be made of ABS—Red and have a finish designated as SPI-A2. Of course, other materials and/or finishes may be utilized, without leaving the scope of the invention. Additionally, by way of non-limiting example, the trigger 50 may have an overall length that is approximately 0.9" (i.e., between portions 50b and 50c). Moreover, the trigger 50 may even be made of a plurality of sections of parts which are joined together to form the complete trigger 50, without leaving the scope of the invention, although it is preferred that it be formed a one-piece member. It would be even more preferable if the trigger 50 were integrally formed with the lancet body, and in particular, integrally formed with the upper body part 10 (see e.g., FIG. 37).

Figure 37:
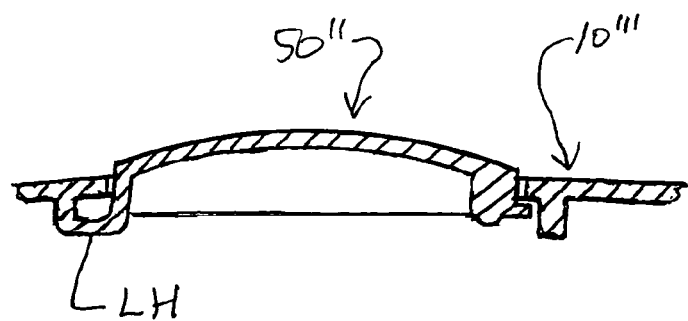
FIG. 37 shows one non-limiting way in which the trigger can be integrally formed with the upper housing part.

The trigger 50 preferably has a end that includes a front projecting flange 50c. This projection 50c is configured to contact an inner surface of upper body part 10 (see FIG. 9) and serves to align the trigger 50 in the trigger opening 10b. The trigger 50 also has a rounded projection 50d. This rounded projection 50d is configured to contact an upper surface of deflecting member 30d of the holding member 30 (see FIG. 15) upon movement of the trigger 50, and specifically, when the trigger 50 is pressed into the lancet device. The projection 50d may have a radius of approximately 0.03". The trigger 50 also includes a rear connecting member 50b which connects the push button 50a to the support flange 10i. As explained previously, this flange 10i is configured to act as a bearing support for the trigger 50. In this regard, a flange opening 10j should be sized to be the same or slightly larger than the width of projection 50b. In this way, the projection flange 50b can fit snugly in the support opening 10j so as to allow the trigger 50 pivot inwards and to return to an armed position. By way of non-limiting examples, the lancet device shown in FIGS. 1-15 can also be modified to use the trigger arming prevention system shown in FIGS. 32 and 33, whereby the trigger 50 can be prevented from returning to the armed position by a trigger stop projection TSP or it can be integrally formed with the upper body part as is shown in FIG. 37.

The push button 50a preferably has a tear-drop or oval shape and includes a inwardly curved (i.e., concave) surface 50f that has a radius of approximately 0.50". The thickness of the projection members 50b and 50c (measured in the direction of FIG. 13A) can be approximately 0.02". These projections members 50b and 50c also act to limit the upward movement of the push button 50a by contacting an inner surface of the upper body 10 when the trigger 50 is in the original non-deflected position (see e.g., FIG. 9). The push button 50a can have curved front and rear edges (see FIG. 13B) whose radius can be approximately 0.15". Finally, the curved outer surface can also include a texture or other high friction surface (not shown) to prevent a user's finger from slipping off of the button 50a.

As explained above with regard to FIG. 1, the trigger 50 is designed to preferably deflect inwardly when a user pushes against the push button 50a (see FIG. 15) and to return to an original position (see FIG. 9). In this regard, the deflection occurs in the area between projection 50b and a connecting projection 10i. The design is such that the material properties of the connection 50b/10j/10i allows the trigger 50 to act like a natural spring.

Figure 14:
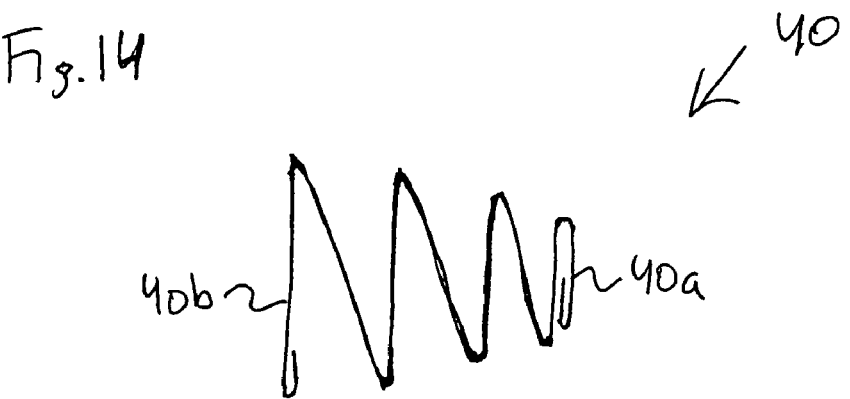
FIG. 14 shows an enlarged side view of the spring used in the embodiment shown in FIG. 1.

FIG. 14 shows the spring 40. By way of non-limiting example, the spring 40 can be made of a wire spring steel and can have the form of a tapered helical coil spring. Of course, the spring 40 can be of any desired type, material and configuration provided it functions for its intended purpose. As explained above, the spring 40 causes (and/or biases) the holding member 30 to move towards an extended position once a trigger 50 is activated. The spring 40 has a smaller diameter end 40a which is secured between flanges 30g and 30f of the holding member 30 and a larger diameter end 40b which is secured to the lancet body via flanges 10f and 20f. Thus, the smaller end 40a is axially retained between a small diameter shoulder 30g and a large diameter shoulder 30f (see FIGS. 12A and 12B). The larger diameter end 40b is axially retained and/or connected to projecting flanges 10f of the lancet body. The spring 40 also causes (and/or biases) the holding member 30 to move back towards an intermediate position (see FIG. 5) after the lancet needle reaches the extended position (see FIG. 4). In this way, the lancet needle LN (and holding member 30) is automatically retracted after puncturing the skin of a user.

FIGS. 16-19 show a second non-limiting embodiment of a single-use and/or disposable lancet device LD. Lancet device LD has a lancet body made up of an upper or front body portion 10 and a lower or rear body portion 20 as with the embodiment shown in FIGS. 1-15, and includes essentially the same parts as those used in the embodiment shown in FIGS. 1-15. However, this embodiment also utilizes a twist-off tab member 70. The tab member 70 may be of the type utilized in, e.g., U.S. Pat. No. 6,514,270. The tab 70 includes a gripping portion 70a and a lancet needle receiving portion 70b (see FIG. 18). The purpose of the tab 70 is to provide protection for the lancet needle, to assure the user that the lancet device has not been used previously, and to allow the user to arm the lancet device. Thus, for example, a user may obtain the lancet device in the arrangement shown in FIGS. 16-18. Then, when the user desires to arm the lancet device for use, the user need only set the cam disk 60 to a desired depth setting, to push the tab 70 into the lancet body to arm the trigger 50 (see FIG. 19), and then to remove and discard the tab 70 by twisting and/or pulling it out of the lancet body. The lancet device will then have the form and/or arrangement shown in FIG. 9 and will be ready for use a single time.

With the removal and discarding of the protective tab 70, the lancet device will not be usable again after it is triggered. This is because the device has no mechanism for rearming the trigger 50. That is, after triggering (and with the tab 70 discarded), a user (or other persons) will be unable to push the holding member 30 backwards into the lancet body until the stop surface 30e engages stop surface 10g. Instead, the lancet device is rendered useless after a single use. Thus, the embodiment shown in FIGS. 16-19 (like the embodiment shown in FIGS. 1-15) provides for a system that prevents rearming of the trigger 50 and/or of the holding member 30 and ensures that the lancet device is a single-use and/or disposable lancet device LD. Whereas the embodiment shown in FIGS. 1-15 provides for a lancet device which is armed in a factory environment, so that the lancet device is rendered usable by a user as soon as he opens its packaging, the device in FIGS. 16-19 provides for a lancet device which can be armed by a user in a simple and safe manner a single time prior to use. This latter configuration may be beneficial because a user can be ensured that the device is not prone to be accidentally triggered (which may occur during shipping). This embodiment also provides greater assurance to the user that the device has not be used previously.

Figure 20:
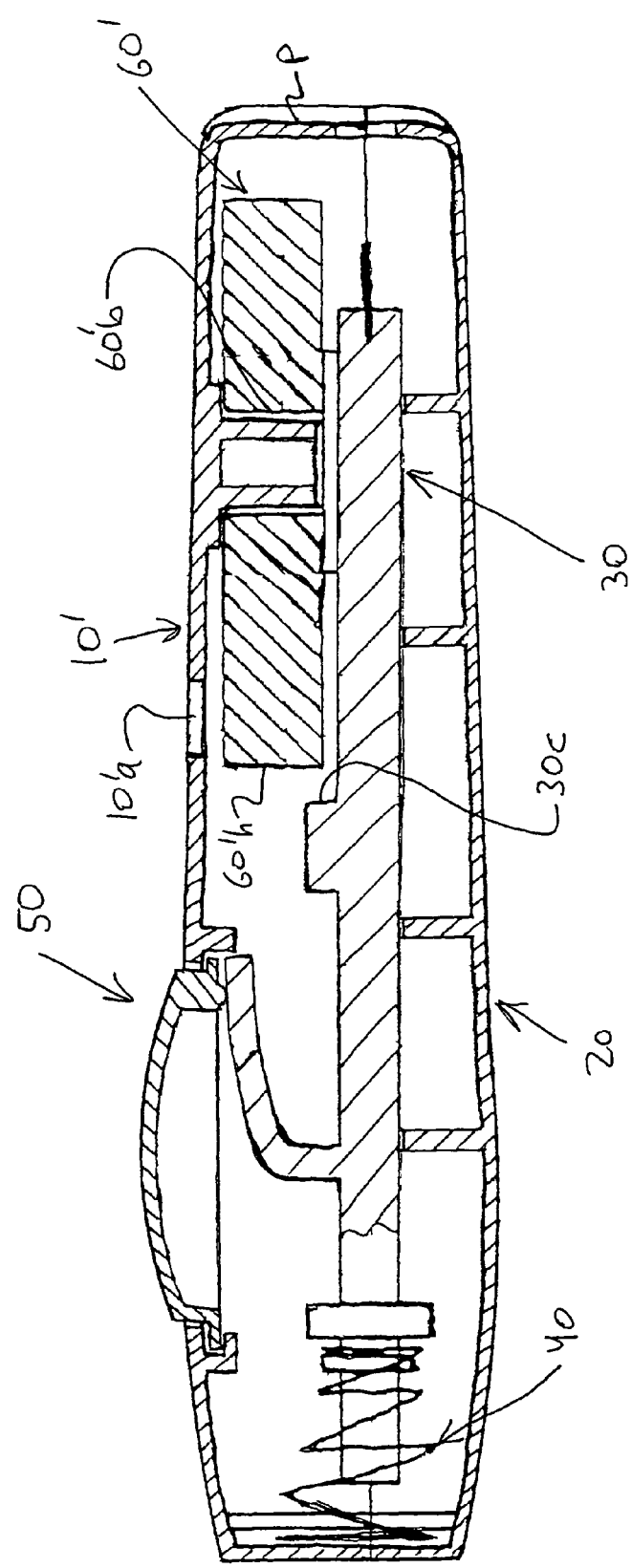
FIG. 20 shows another enlarged side cross-section view of still another embodiment of a single-use lancet device. The device is shown with the lancet holding member in an armed and/or fully retracted and/or trigger-set position. In this embodiment, the cam disk of the type shown in FIG. 1 has been replaced with a cam disk which has a generally circular circumference and whose center opening is off-set from a center axis of the cam disk.
Figure 21:
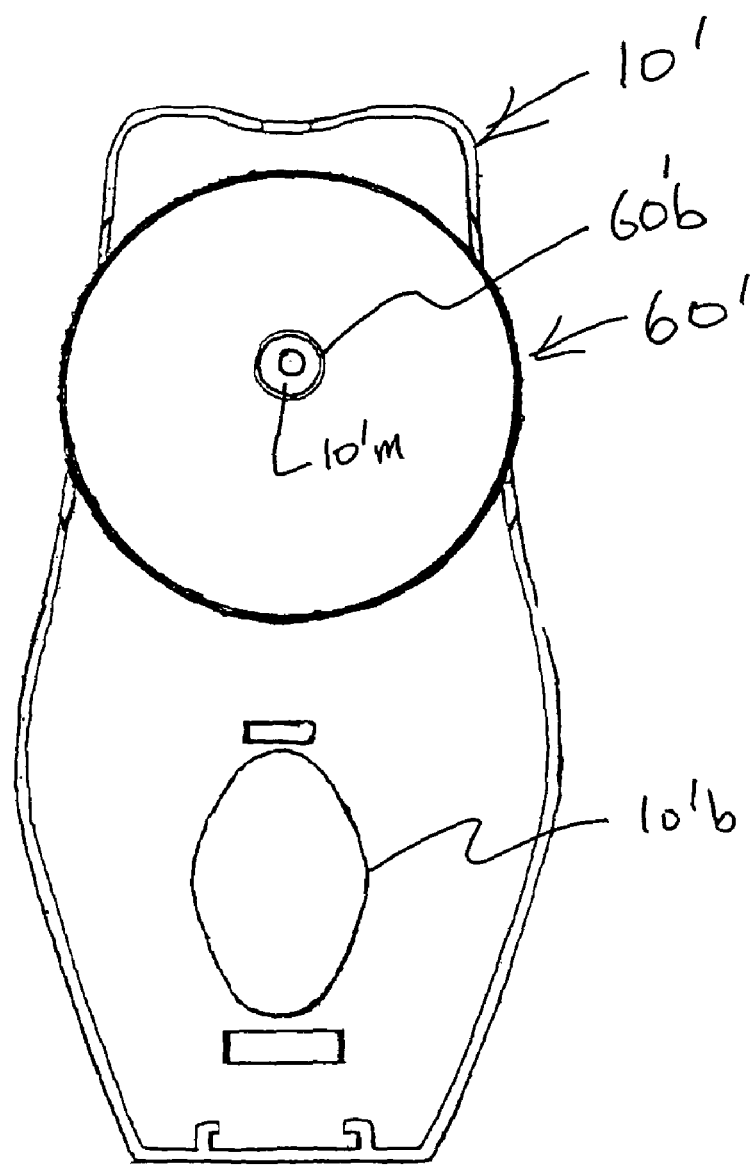
FIG. 21 shows a rear side view of the embodiment shown in FIG. 20. The device is shown with the rear cover removed thereby exposing the inside of the front cover. The trigger has been removed and the cam disk is shown rotatably mounted to the front cover.
Figure 22:
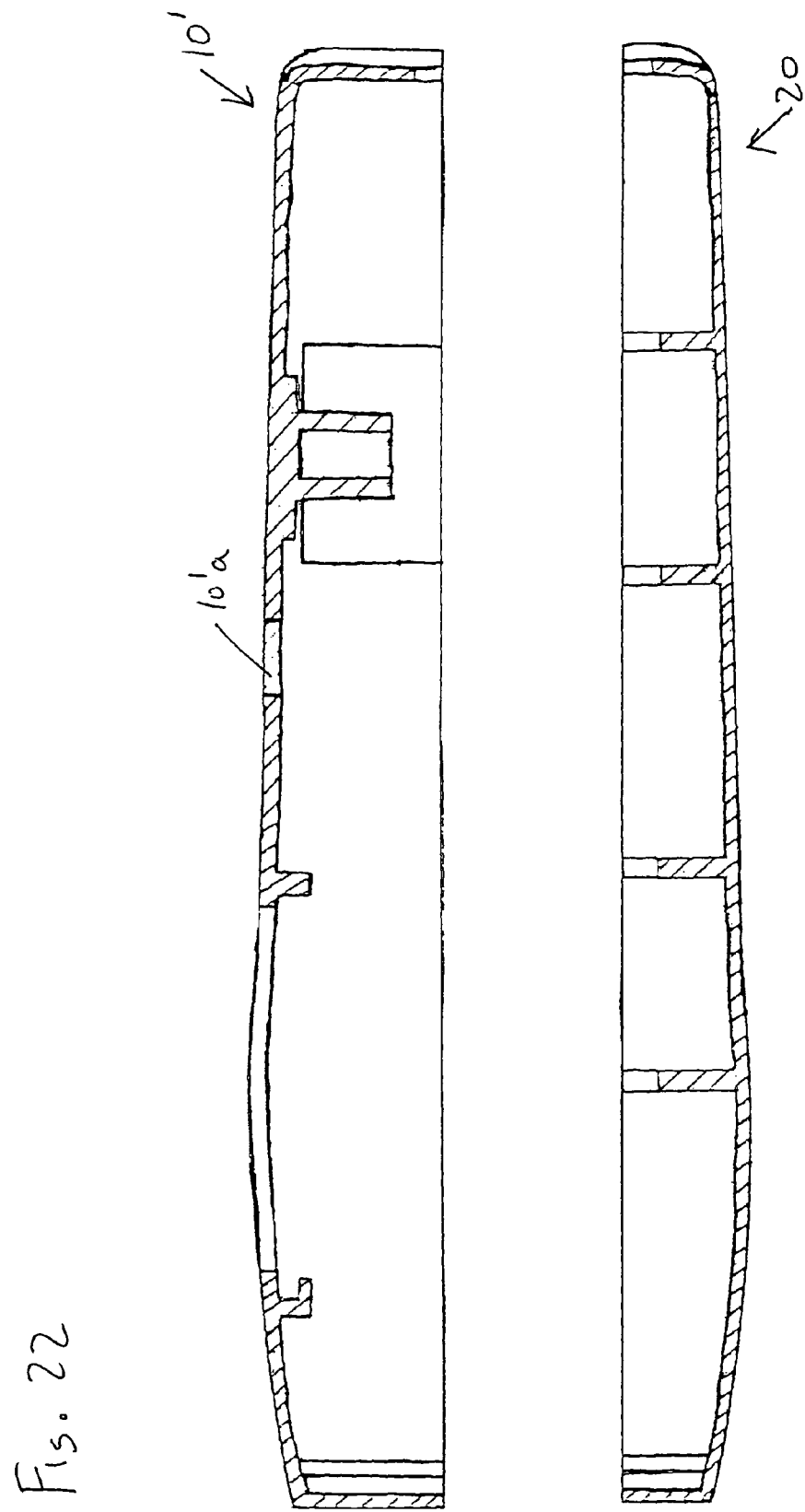
FIG. 22 shows another enlarged side cross-section view of the embodiment shown in FIG. 20. The device is shown with lancet holding member, trigger, spring and cam disk removed to expose an inside of the front and rear cover members. The front and rear covers are shown separated from each other.

FIGS. 20-22 show a third non-limiting embodiment of a single-use and/or disposable lancet device LD. Lancet device LD has a lancet body made up of an upper or front body portion 10' and a lower or rear body portion 20. The trigger 50, spring 40, lancet holding member 30, and lower body portion 20 are substantially similar to the corresponding parts of the embodiment shown in FIGS. 1-15. However, the upper body part 10' and cam disk 60' are different from the ones used in the embodiment shown in FIGS. 1-15. In this embodiment, the upper body part 10' lacks the projection 10k and uses a cam disk 60' whose axle opening 60'b is off-set from a center of the cam disk 60'. Moreover, unlike the cam disk used in the embodiment shown in FIGS. 1-15, the cam disk 60' used in this embodiment lacks the planar cam surfaces 60e1-60e8 and instead utilizes a continuous peripheral cam surface whose distance varies from a center axis of the journal 10'm.

On the other hand, the operation of the cam disk adjustment is similar because rotation of the cam disk 60' to different depth setting positions allows the stop surface 30c to contact different portions of the peripheral cam surface 60'h, thereby adjusting the depth of the lancet needle past the plane P.

Figure 25:
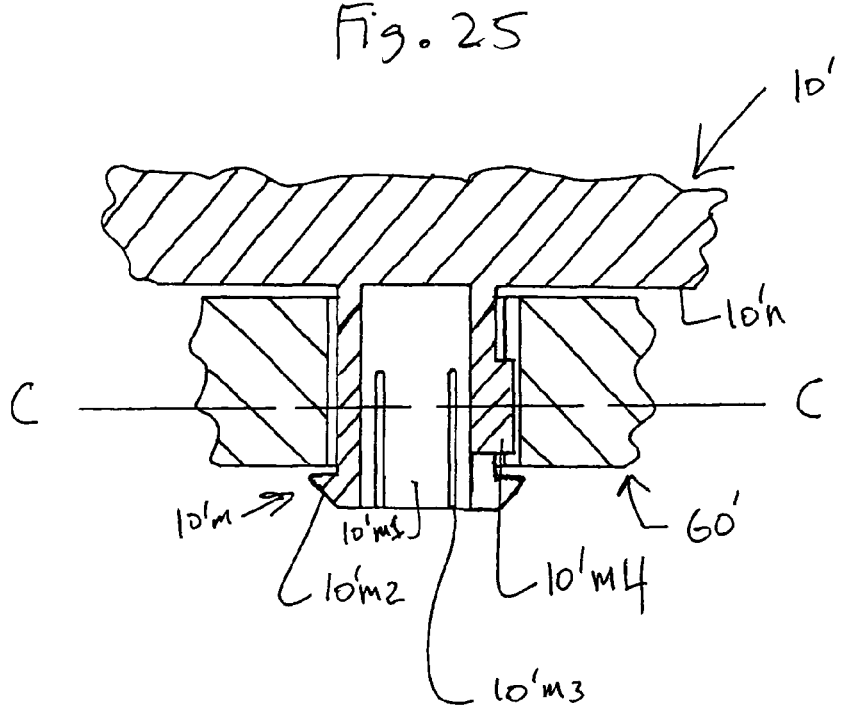
FIG. 25 shows an enlarged partial cross-section view of one way in which the cam disk used in the embodiments shown in FIGS. 20-23 can be rotatably mounted to the front cover member.
Figure 26:
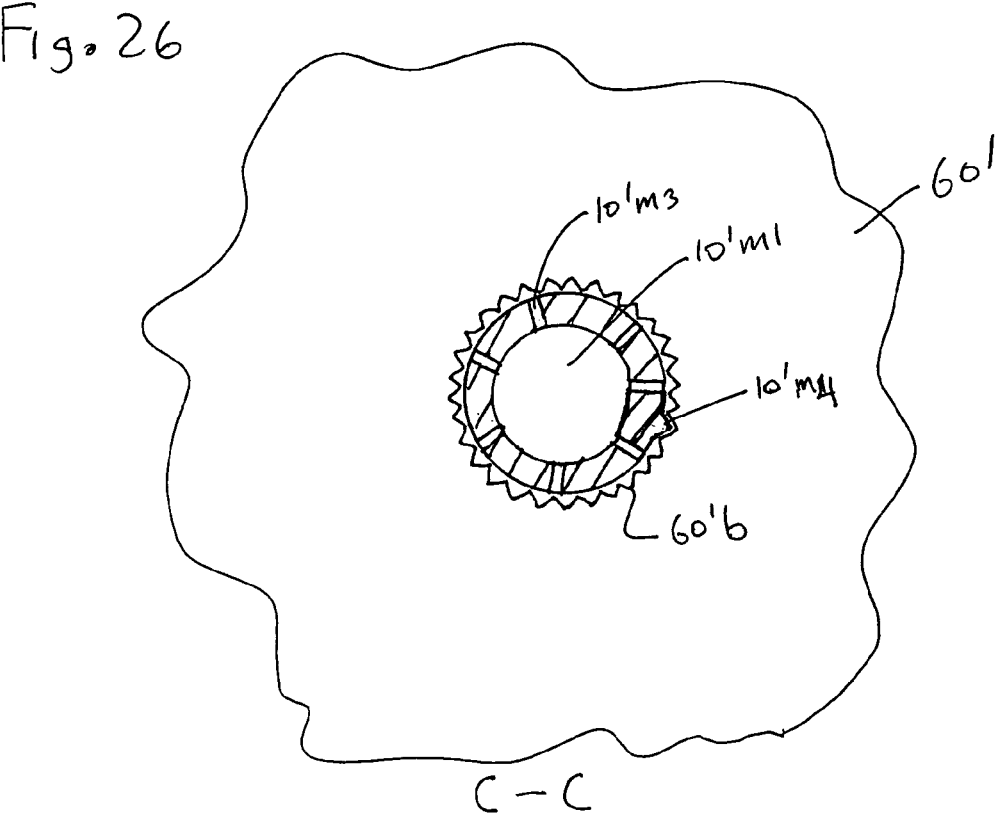
FIG. 26 shows an enlarged partial cross-section end view of section C-C shown in FIG. 25.
Figure 27:
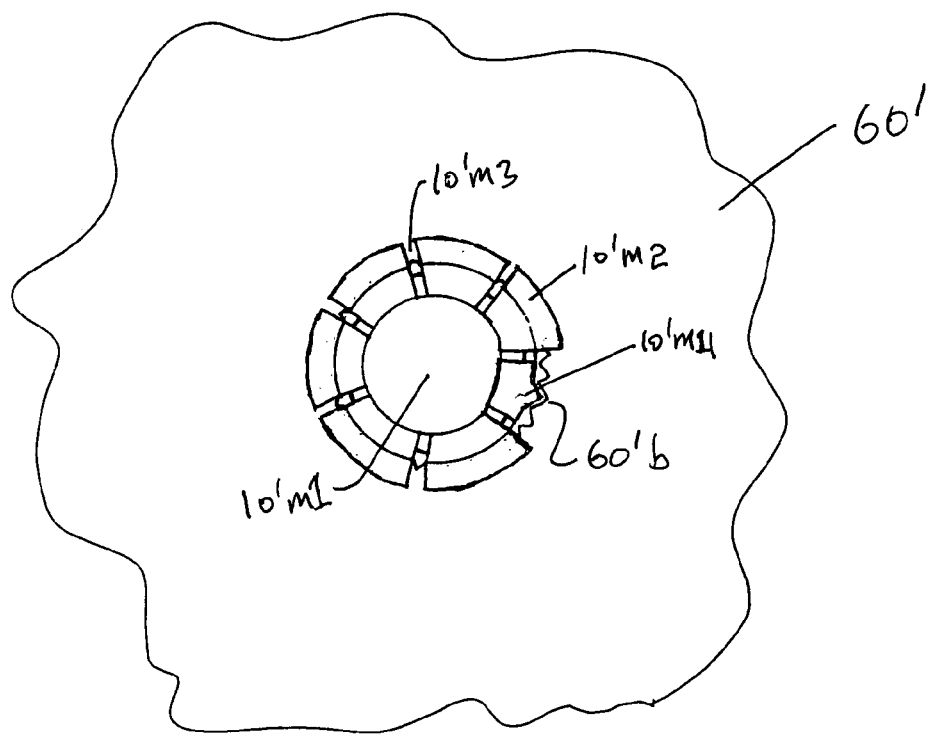
FIG. 27 shows an enlarged partial end view of FIG. 25.

In order to ensure that the cam disk 60' is retained in a desired depth setting, the opening 60'b can include notches and projections which are engaged by a tooth 10'm4 (see FIGS. 25-27). The cam disk 60' is retained on the journal 10'm between surface 10'n (similar to surface 10n of FIG. 7) and a plurality of projections 10'm2 which are separated by slots 10'm3. The slots 10'm3 allow the projections 10'm2 to deflect inwards when the cam disk 60' is snapped onto the journal 10'm during assembly. They also allow the tooth 10'm4 to deflect in and out as it engages with the notches/projections 60'b of the cam disk 60'. As a non-limiting alternative to the cam disk connecting system shown in FIGS. 25-27, the cam disk 60' used in the embodiment shown in FIGS. 20-22 can instead utilize the connection system shown in FIG. 29 wherein a retaining member 80' is used to axially retain the cam disk 60' on the journal 10"m. The retaining member 80' frictionally engages with the opening 10"m1. As with the connection system used in FIGS. 25-27, the connection system used in FIG. 29 utilizes slots 10"m3 and a tooth 10"m4 to engage with notches/projections 60'b of the cam disk 60'. In this way, the cam disk 60' is axially retained between surface 10"n and the head of retaining member 80'. The device can otherwise operate in a manner similar to that described with regard to the embodiment shown in FIGS. 1-15.

Figure 23:
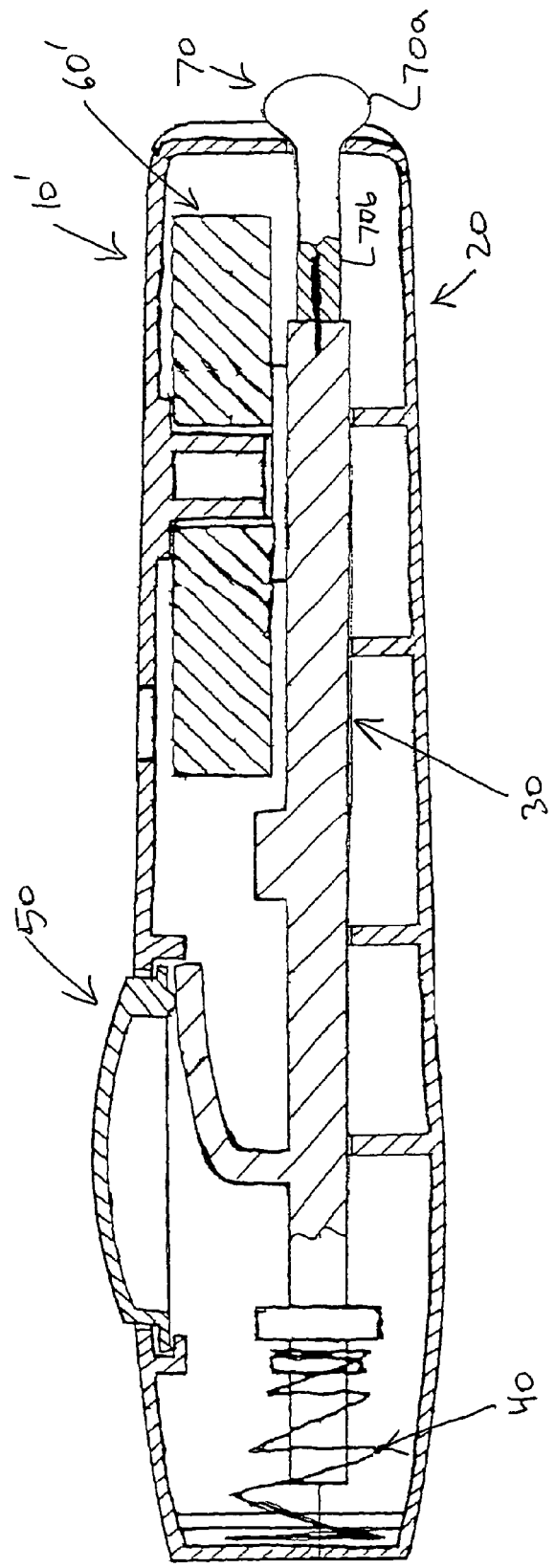
FIG. 23 shows an enlarged side cross-section view of still another embodiment of the single-use lancet device. The device is shown with a tab having caused the lancet holding member to move to the armed and/or fully retracted and/or trigger-set position. All of the parts used in this embodiment are of the same type as the parts used in the embodiment shown in FIG. 20, except that this embodiment also utilizes a twist-off tab.

FIG. 23 show a fourth non-limiting embodiment of a single-use and/or disposable lancet device LD. Lancet device LD has a lancet body made up of an upper or front body portion 10' and a lower or rear body portion 20 as with the embodiment shown in FIGS. 20-22, and includes essentially the same parts. However, this embodiment also utilizes a twist-off tab member 70. The tab member 70 may be of the type utilized in, e.g., U.S. Pat. No. 6,514,270. The tab 70 includes a gripping portion 70a and a lancet needle receiving portion 70b. The purpose of the tap 70 is to provide protection for the lancet needle, to assure the user that the lancet device has not been used previously, and to allow the user to arm the lancet device. Thus, for example, a user may obtain the lancet device in an unarmed position similar to that shown in FIG. 18. Then, when the user desires to arm the lancet device for use, the user need only set the cam disk 60' to a desired depth setting, to push the tab 70 into the lancet body to arm the trigger 50 (in the same way shown in FIG. 19), and then to remove and discard the tab 70 by twisting and/or pulling it out of the lancet body. The lancet device will then have the form and/or arrangement shown in FIG. 20 and will be ready for use.

With the removal and discarding of the tab 70, the lancet device will not be usable again. As with previously described embodiments, the device has no mechanism for rearming the trigger 50 once the trigger 50 releases the holding member 30. That is, without the tab 70, a user (or other person(s)) will be unable to push the holding member 30 backwards into the lancet body until the stop surface 30e engages stop surface 10g. Instead, the lancet device is rendered useless after a single use. Thus, the embodiment shown in FIG. 23 (like the embodiment shown in FIGS. 16-19) provides for a system that prevents rearming of the trigger 50 and/or of the holding member 30, and ensures that the lancet device is a single-use and/or disposable lancet device LD. Whereas the embodiments shown in FIGS. 1-15 and 20-22 provide for lancet devices which can be armed in a factory environment so that the lancet device is rendered usable by a user as soon as he opens its packaging, the device in FIG. 23 (as with the device shown in FIGS. 16-19) provides for a lancet device which can be armed by a user in a simple and safe manner only a single time. This latter configuration may be beneficial because a user can be ensured that the device is not prone to be accidentally triggered, e.g., during shipping. This embodiment also provides greater assurance to the user that the device has not be used previously.

Figure 30:
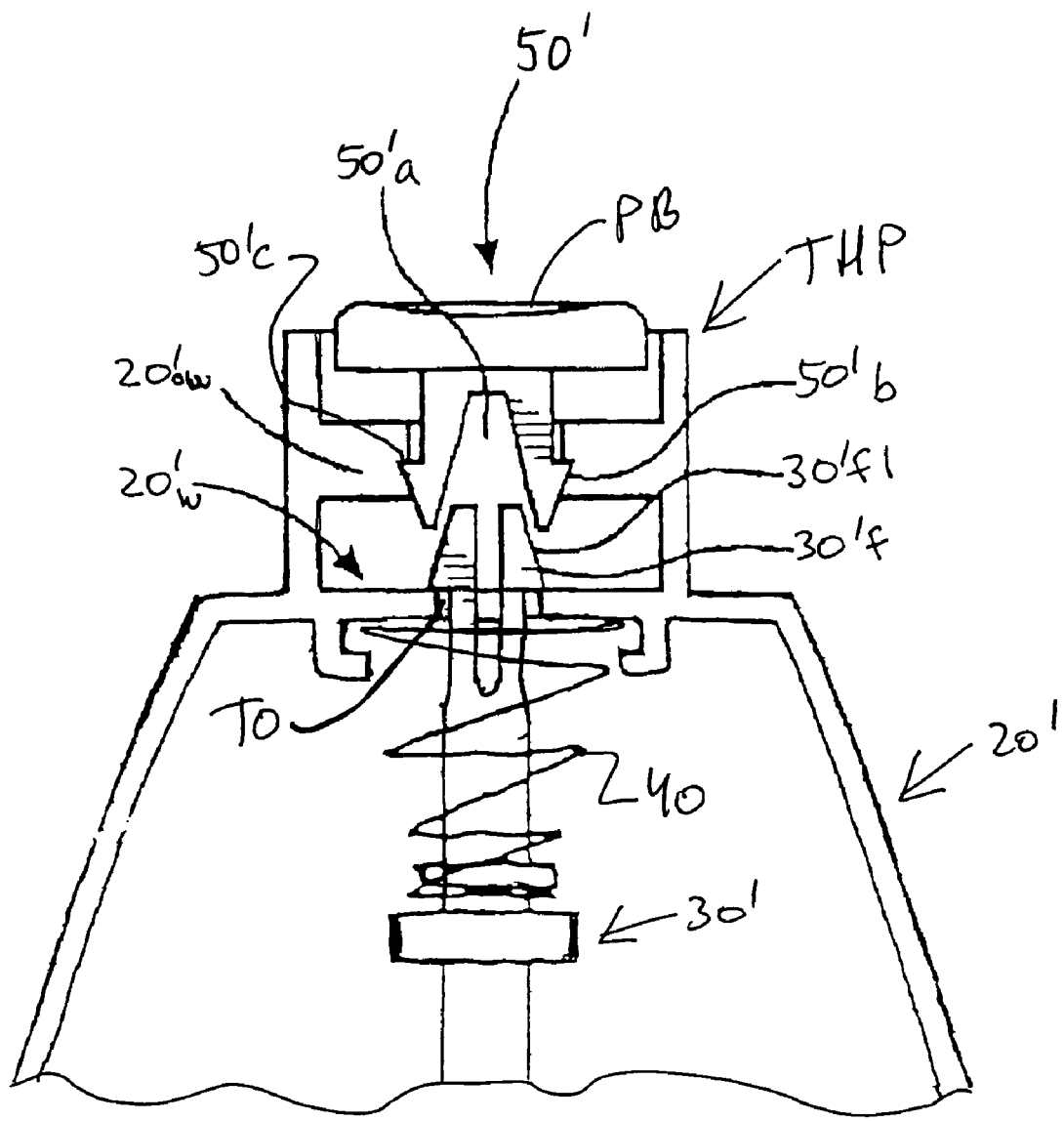
FIG. 30 shows a partial view of still another embodiment of a single-use lancet device. This embodiment is similar to that of FIG. 1, except that the side trigger is replaced with a rear trigger system and except that a modified lancet holding member is utilized.

FIG. 30 shows a partial view of still another non-limiting embodiment of a single-use lancet device. This embodiment is similar to that of FIG. 1, except that the side trigger is replaced with a rear trigger system and except that a modified lancet holding member is utilized. This trigger arrangement can be used on any of the embodiments disclosed herein. The upper and lower housing parts (only the lower housing part 20' is shown) and also modified to include a trigger housing portion THP. The holding member 30' is similar to the holding member 30 used in the previous embodiments. However, in this disposable lancet device embodiment, the holding member 30' includes a rear portion with a plurality of flexible fingers 30'f, e.g., two, three or four fingers 30'f. These fingers 30'f are separated by one or more slots 30'f3 (see FIG. 31). Each finger 30'f has a tapered outer surface 30'f1 and an engaging surface 30'f2 which projects through an opening TO in the wall, e.g., wall 20'w, of the two housing parts. The engaging surfaces 30'f2 are configured to engage the wall (as is shown in FIG. 30) of the housing parts when they are assembled to each other (only the lower housing part 20' is shown). As can be seen in FIG. 30, when the holding member 30' is in the armed position, the engaging portions 30'f2 of the fingers 30'f engage the housing wall 20'w and prevent the holding member 30' from moving under the biasing force of the spring 40 towards the extended position.

However, when a user desires to cause puncturing of the skin, the user need only place the plane P of the device against the skin and apply a force to the trigger 50'. This will cause its movement towards the holding member 30'. In this regard, the trigger 50' includes push button portion PB and a plurality of projecting fingers separated by a tapered opening 50'a. These fingers include tapered outer surfaces 50'b which engage outer walls of the housings (only outer wall 20'ow of the lower housing is shown). As the trigger 50' is moved towards the holding member 30', the tapered opening 50'a of the fingers engages with the tapered surfaces 30'f1 of the fingers 30'f. This, in turn, causes the fingers 30'f to deflect inwardly towards each other until the engaging surfaces 30'f2 no longer engage with the housing walls, e.g., 20'w. At this point, the spring 40 is free to move the holding member 30' towards the extended position in the same way as the previous embodiments. However, because of the trigger design shown in FIG. 30, the trigger 50' will be prevented from assuming the position shown in FIG. 30 after it has triggered the movement of the holding member 30'. This is because the trigger fingers, and more specifically the projections 50'b include surfaces 50'c which engage with lower surfaces of the outer walls, e.g., outer wall 20'ow. Such engagement will prevent the trigger 50' from moving back up to the armed position. In this way, the arrangement shown in FIG. 30 constitutes a system which renders the lancet device to be a single-use or disposable lancet device. U.S. Pat. No. 6,514,270, the disclosure of which has been expressly incorporated by reference in its entirety, describes a similar system.

Figure 31:
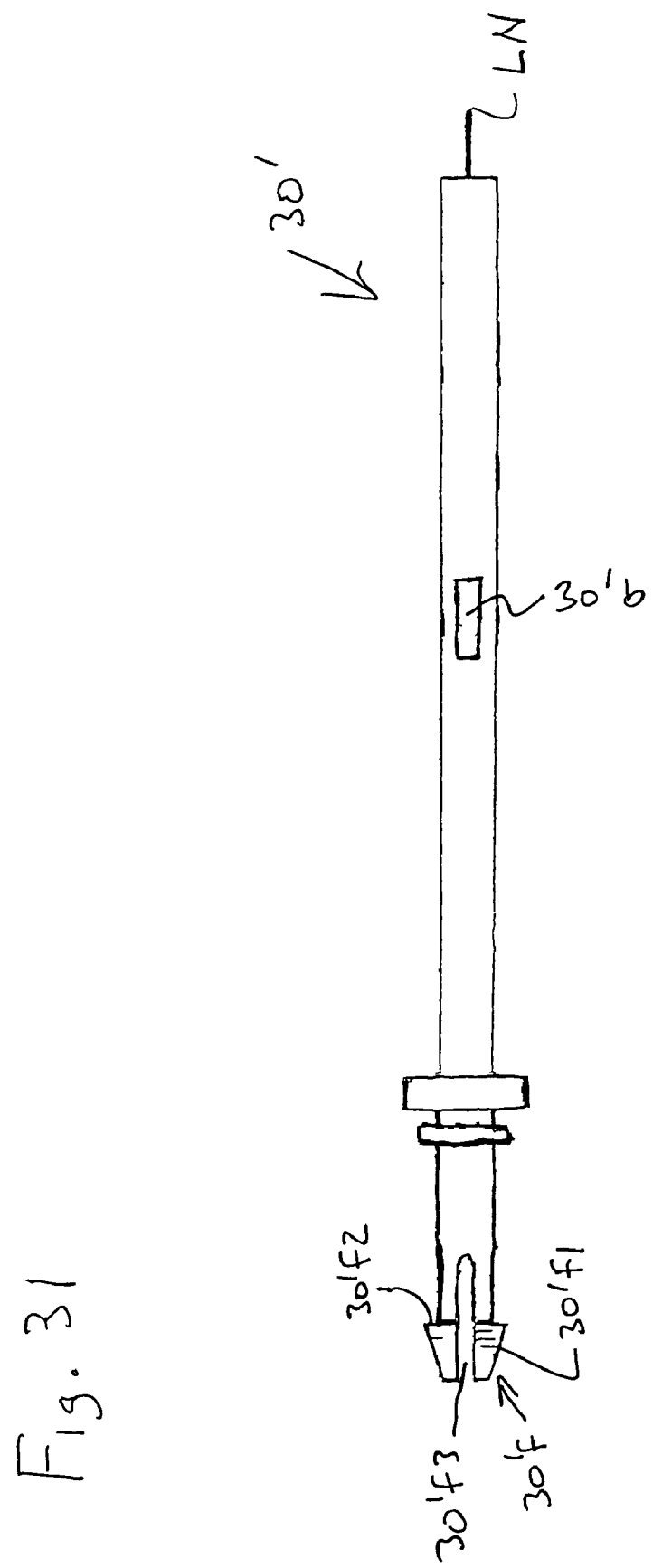
FIG. 31 shows a side view of the modified lancet holding member of FIG. 30.

FIG. 31 shows the holding member 30' used in the embodiment of FIG. 30. This figure makes clear that the holding member 30' is similar to the holding member 30 used in the previous embodiments, except that it dispenses with the deflecting member and further includes a rear portion with fingers 30'f and one or more slots 30'f3. As explained above, the fingers 30'f include tapered outer surfaces 30'f1 and engaging surfaces 30'f2. As with the previous embodiments, the stop projection 30'b engages with a cam disk 60 or 60' in the same way as with the previous embodiments.

Figure 32:
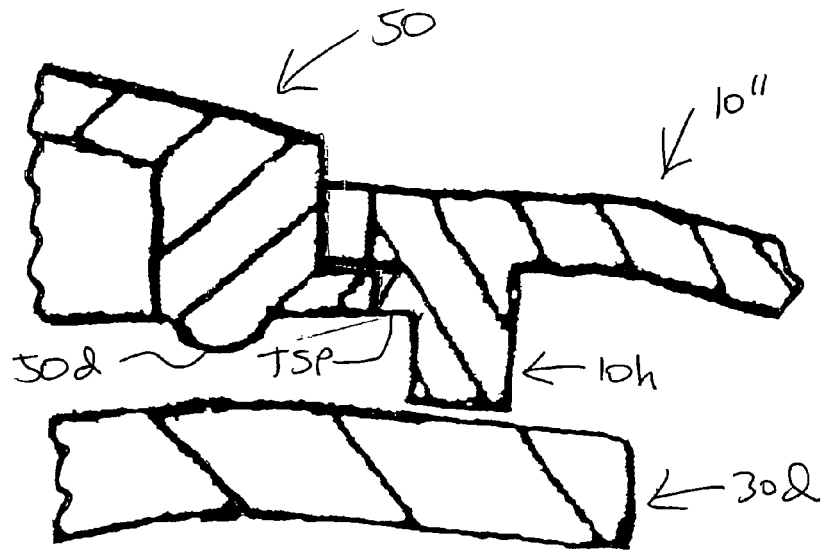
FIGS. 32 and 33 show one non-limiting way in which the lancet device can be prevented from being re-armed.
Figure 33:
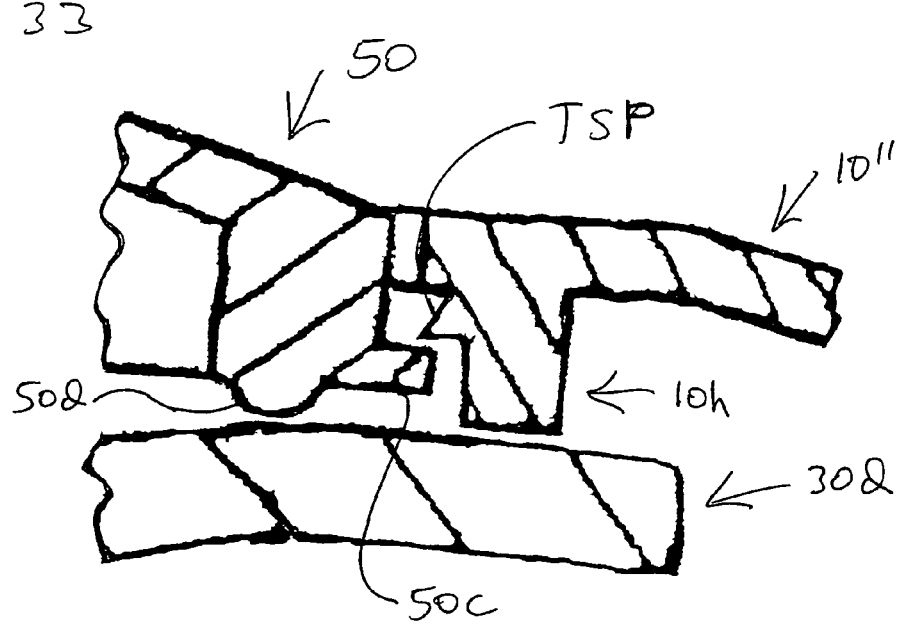

FIGS. 32 and 33 show one non-limiting way in which the lancet devices shown in FIGS. 1-29 can be modified. In this modification, the upper housing part 10" can be similar to housing parts 10 and 10' except they can further include an integrally formed trigger stop projection TSP. As can be seen in comparing FIGS. 32 and 33, the trigger stop projection TSP prevents the trigger 50 from being re-armed, i.e., from assuming an original armed position. As is evident from FIG. 33, the projection TSP will engage with projection 50c (thereby limiting its upward movement) when the trigger 50 tries to move back up to the position shown in FIG. 32. This arrangement also prevents the deflecting member 30d from again engaging with the stop projection 10h. In this way, the arrangement shown in FIGS. 32 and 33 constitutes still another system which renders the lancet device to be a single-use or disposable lancet device.

Figure 34:
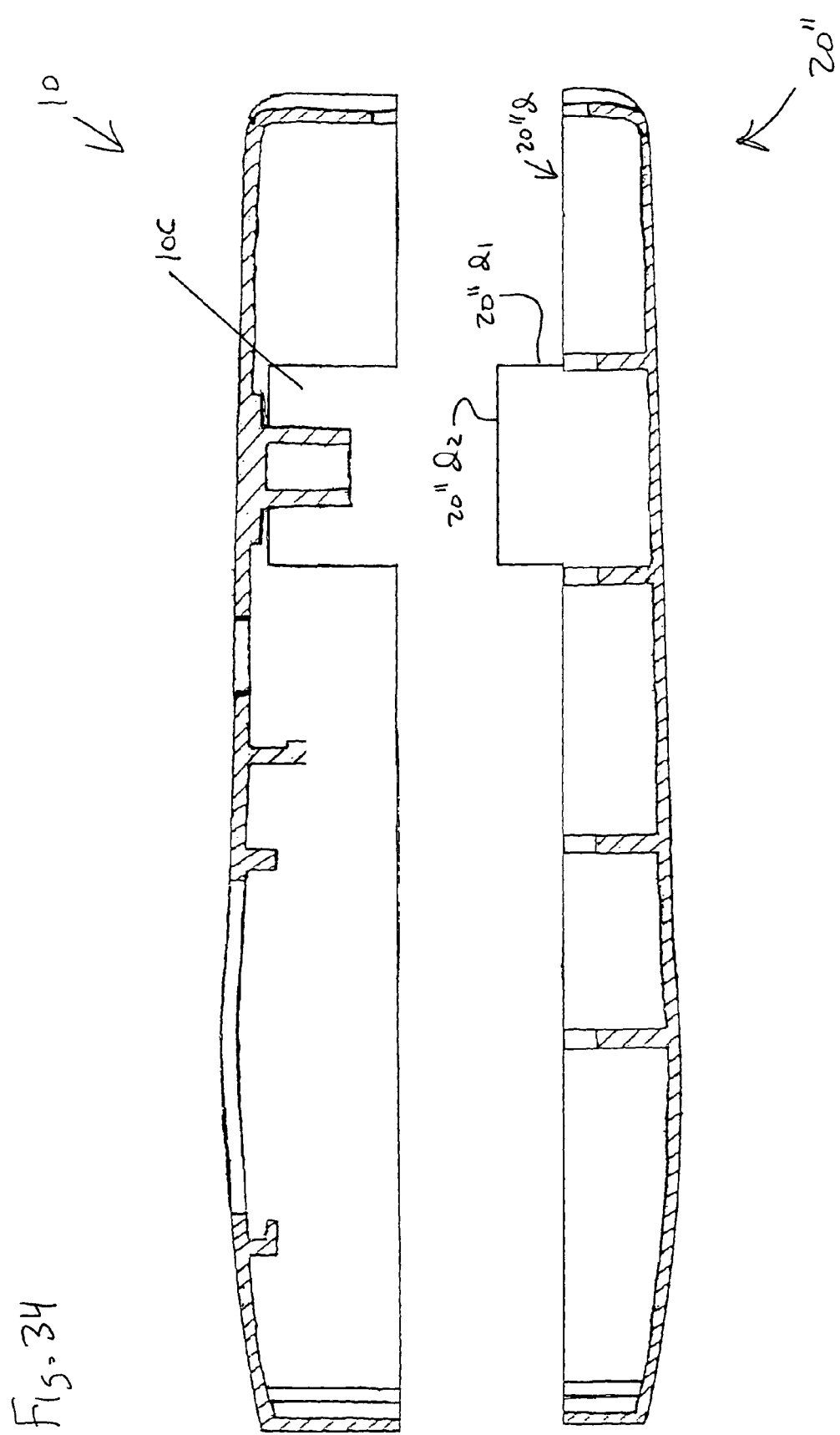
FIG. 34 shows a side cross-section view of a modified lancet body. The body can utilize the same internal parts and the upper cover as the embodiment shown in FIGS. 1-15. However, the lower cover includes two projecting walls which slide into the side openings of the upper cover.

FIG. 34 shows one non-limiting variation of the upper and lower housing parts 10 and 20'''. Such a housing arrangement can replace the ones used on the lancet devices shown in FIGS. 1-29, 32 and 33. However, the housing arrangement in FIG. 34 is specifically designed to replace housings 10 and 20 of the embodiment shown in FIGS. 1-19. In this modification, the upper housing part 10 is essentially the same that the housing part 10. Lower housing part 20''' is similar to housing 20 except that is includes two oppositely arranged integrally formed projecting walls (only one projecting wall is visible). As is evident from FIG. 34, the projecting walls include an upper edge 20"d2 and two side edges 20"d1. The projecting walls are sized and shaped to fit within openings 10c in the upper housing part 10. When assembled together, the upper and lower housing parts 10 and 20", and more specifically the upper end of opening 10c and the upper edge 20"d2 of wall 20"d, form window openings or side openings which are sized to allow portions of the cam disk 60 to project therethrough. Such an overlapping housing arrangement can be used on any of the embodiments disclosed herein.

Figure 35:
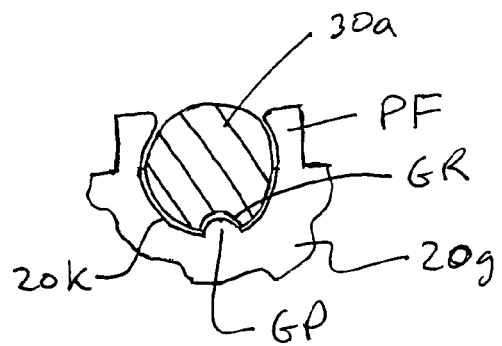
FIG. 35 shows one non-limiting way in which a circular holding member can be movably retained by the lower housing part.

FIG. 35 shows one non-limiting way in which a circular holding member can be movably retained by the lower housing part 20. The holding member 30 includes guiding recess GR which receives therein a guiding projection GP that is integrally formed with the projecting walls 20g-20j (only wall 20g is shown). The walls 20g-20j and include projecting fingers PF which allows the holding member 30 to be snapped into place in the recesses 20k-20n (only recess 20k is shown). This arrangement allows the holding member 30 to move axially within the lancet device without while being prevented from rotating. The arrangement also prevents the holding member 30 from moving up and out of engagement with the lower housing part 20. This holding member guiding arrangement can be used on any of the embodiments disclosed herein.

Figure 36:
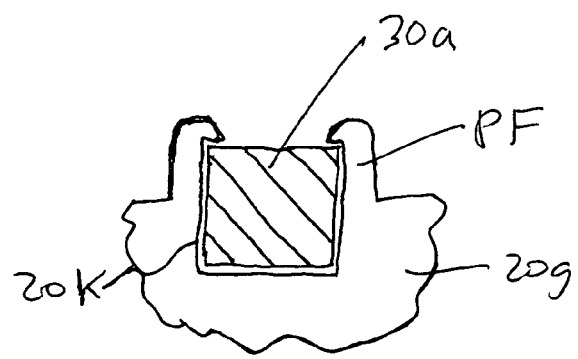
FIG. 36 shows one non-limiting way in which a polygonal or square shaped holding member can be movably retained by the lower housing part.

FIG. 36 shows another non-limiting way in which a polygonal shaped holding member can be movably retained by the lower housing part 20. The holding member 30 includes planar sides which correspond to guiding surfaces of the recess which is integrally formed with the projecting walls 20g-20j (only wall 20g is shown). The walls 20g-20j and include projecting fingers PF which allows the holding member 30 to be snapped into place in the recesses 20k-20n (only recess 20k is shown). This arrangement allows the holding member 30 to move axially within the lancet device without while being prevented from rotating. The arrangement also prevents the holding member 30 from moving up and out of engagement with the lower housing part 20. This holding member guiding arrangement can be used on any of the embodiments disclosed herein.

FIG. 37 shows one non-limiting way in which the trigger 50" can be integrally formed with the upper housing part 10'''. Instead of the bearing system 10i/10j/50b, this trigger connection utilizes a living hinge LH to connect the trigger 50" to the upper housing part 10'''. This trigger arrangement can be used on any of the embodiments disclosed herein, except for the embodiment shown in FIG. 30.

All the parts of the lancet device, with the exception of the spring 40 (which can be made of spring steel) and with the exception of the lancet needle (which can be a conventional metal needle mounted to a conventional plastic lancet 10), may be made from plastic materials and can be formed using conventional injection molding techniques or other known manufacturing methods. The cam disk for example can be integrally formed with peripheral grooves and/or projections (similar to a coin), and with the indicating marks. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A single-use lancet device, comprising:
 a body comprising a skin engaging end that includes a lancet opening through which a lancet needle extends;
 a trigger mounted to the body;
 a holding member movably mounted within the body and comprising a front end and a rear end;
 the holding member being movable between a retracted position and an extended position;
 a stop surface that moves with the holding member;
 a cam disk comprising cam surfaces which can be contacted by the stop surface; and
 the cam disk being configured to rotate at least partially about an axis that is not parallel to an axis running through at least one of the lancet opening and the holding member,
 wherein, once caused to move to the extended position by the trigger, the holding member is prevented from moving back to the retracted position, and
 wherein the single-use lancet device is usable for forming a skin puncture only once.

2. The lancet device of claim 1, further comprising a spring, wherein the spring causes the holding member to move to the extended position and prevents the holding member from moving back to the retracted position.

3. The lancet device of claim 1, further comprising a compression spring for biasing the holding member towards an extended position.

4. The lancet device of claim 3, wherein the spring comprises one end that is fixed to the holding member and another end that is fixed to the body.

5. The lancet device of claim 3, wherein the spring comprises one end that is connected to the holding member and another end that is connected to the body.

6. The lancet device of claim 1, wherein the trigger is movably mounted to the body.

7. The lancet device of claim 1, wherein the body comprises an upper housing part and a lower housing part.

8. The lancet device of claim 1, wherein the holding member comprises a projection that includes the stop surface.

9. The lancet device of claim 1, wherein the holding member comprises an integrally formed projection that includes the stop surface.

10. The lancet device of claim 1, wherein the front end comprises the lancet needle.

11. The lancet device of claim 1, further comprising a deflecting member configured to be deflected by the trigger.

12. The lancet device of claim 11, wherein the deflecting member is coupled to the holding member.

13. The lancet device of claim 11, wherein the deflecting member comprises a stop surface that contacts a surface of a holding projection extending inwardly from the body.

14. The lancet device of claim 1, wherein the cam disk comprises indicia.

15. The lancet device of claim 14, wherein the cam surfaces are arranged on a cam section of the cam disk, the cam section being disposed on a side of the cam disk that is opposite a side that includes the indicia.

16. The lancet device of claim 1, wherein the cam disk comprises a centrally disposed opening that is mounted to a journal arranged in the body.

17. The lancet device of claim 16, wherein the journal is coupled to the body.

18. The lancet device of claim 16, wherein the journal extends inwardly from the body.

19. The lancet device of claim 16, wherein the journal comprises a center axis that is generally perpendicular to the axis running through the holding member.

20. The lancet device of claim 1, wherein the cam disk rotates about an axis that is generally perpendicular to an axis running through at least one of the lancet opening and the holding member.

21. The lancet device of claim 1, wherein the cam disk is disposed between the trigger and the skin engaging end.

22. The lancet device of claim 1, wherein the body comprises a two-piece body.

23. The lancet device of claim 22, wherein the cam disk is coupled to one of the two pieces of the two-piece body.

24. The lancet device of claim 1, wherein the body comprises at least one side opening through which a portion of the cam disk protrudes.

25. The lancet device of claim 1, wherein the body comprises two generally oppositely arranged side openings through which portions of the cam disk protrude.

26. The lancet device of claim 1, wherein the body comprises two side openings through which portions of the cam disk protrude.

27. The lancet device of claim 1, wherein the body comprises a mechanism for viewing indicia of the cam disk.

28. The lancet device of claim 27, wherein the mechanism for viewing indicia of the cam disk comprises an opening.

29. The lancet device of claim 1, further comprising a retaining element for one of axially retaining the cam disk and securing the cam disk to the body.

30. The lancet device of claim 29, wherein the cam disk comprises a centrally disposed opening that is mounted to a journal arranged in the body and further comprising a retaining element for one of axially retaining the cam disk and securing the cam disk to the journal.

31. A method of puncturing a surface of skin using the lancet device of claim 1, the method comprising:
    adjusting a set depth of penetration of the lancet needle by moving the cam disk to a desired set position;
    disposing the skin engaging end of the lancet device against a user's skin;
    triggering the trigger to cause the lancet needle to penetrate the user's skin; and
    preventing the user from moving the holding member to the retracted position,
    wherein the puncture allows a blood sample to be taken.

32. A method of puncturing a surface of skin using the lancet device of claim 1, the method comprising:
    adjusting a set depth of penetration of the lancet needle by moving the cam disk to a desired set position;
    disposing the skin engaging end of the lancet device against a user's skin;
    triggering the trigger to cause the lancet needle to penetrate the user's skin; and
    preventing the user from moving the trigger to an original armed position,
    wherein the puncture allows a blood sample to be taken.

33. A method of using the lancet device of claim 1, the method comprising:
    rotating the cam disk to a desired set position;
    moving the holding member to a retracted position with a removable element;
    removing the removable element from engagement with the lancet needle;
    maintaining the holding member in the retracted position until the trigger is triggered;
    disposing the skin engaging end of the lancet device against a user's skin; and
    triggering the trigger to cause movement of the holding member.

34. A method of using the lancet device of claim 1, the method comprising:
    rotating the cam disk to a desired set position;
    moving the holding member to a retracted position with a removable element;
    removing the removable element from engagement with the front end of the holding member;
    maintaining the holding member in the retracted position until the trigger is triggered;
    disposing the skin engaging end of the lancet device against a user's skin; and
    triggering the trigger to cause movement of the holding member.

35. A single-use lancet device, comprising:
    a body comprising a skin engaging end that includes a lancet opening through which a lancet needle extends;
    a trigger;
    a holding member movably mounted within the body and comprising a front end a rear end;
    the holding member being movable between a retracted position and an extended position;
    a stop projection coupled to the holding member;
    a cam disk comprising indicia and cam surfaces which can be contacted by the stop projection; and
    the cam disk being rotatably mounted to a projection that extends inwardly from the body, wherein, once caused to move to the extended position by the trigger, the holding member is prevented from moving back to the retracted position, and wherein the single-use lancet device is usable for forming a skin puncture only once.

36. A single-use lancet device, comprising:

a body comprising a skin engaging end that includes a lancet opening through which a lancet needle extends;

a trigger;

a holding member movably mounted within the body and comprising a front end a rear end;

the holding member being movable between a retracted position and an extended position;

a stop surface coupled to the holding member;

a circular cam disk at least partially arranged within the body;

the cam disk comprising indicia and cam surfaces which can be contacted by the stop projection; and the cam disk being configured to rotate at least partially and protruding from at least one side wall of the body, wherein, once caused to move to the extended position by the trigger, the holding member is prevented from moving back to the retracted position.

* * * * *